United States Patent [19]
Takashima et al.

[11] Patent Number: 6,037,312
[45] Date of Patent: Mar. 14, 2000

[54] ISOXAZOLE DERIVATIVES

[75] Inventors: Yoriyuki Takashima, Sodegaura; Hideki Kamano, Ichihara; Masashi Sakamoto, Sodegaura, all of Japan

[73] Assignee: Idemitsu Kosan Co., Ltd., Tokyo, Japan

[21] Appl. No.: 09/147,282

[22] PCT Filed: May 21, 1997

[86] PCT No.: PCT/JP97/01704

§ 371 Date: Feb. 3, 1999

§ 102(e) Date: Feb. 3, 1999

[87] PCT Pub. No.: WO97/44340

PCT Pub. Date: Nov. 27, 1997

[30] Foreign Application Priority Data

May 23, 1996 [JP] Japan .................................. 8-128795

[51] Int. Cl.⁷ .......................... A01N 43/80; C07D 261/08
[52] U.S. Cl. ........................................... 504/271; 548/248
[58] Field of Search .............................. 548/248; 504/271

[56] References Cited

FOREIGN PATENT DOCUMENTS

| | | |
|---|---|---|
| 7-149742 | 6/1995 | Japan . |
| WO 93/18031 | 9/1993 | WIPO . |
| WO 94/18179 | 8/1994 | WIPO . |
| WO 96/2541 | 8/1996 | WIPO . |

*Primary Examiner*—Joseph McKane
*Attorney, Agent, or Firm*—Oblon, Spivak, McClelland, Maier & Neustadt, P.C.

[57] ABSTRACT

Isoxazole derivatives of the formula (I),

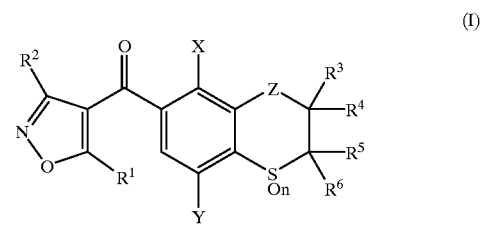

and herbicides containing the above isoxazole derivatives as active ingredients, which can selectively control grass weeds and broad-leaved weeds simultaneously at a low dosage as a single herbicide, without causing phytotoxicity on corn, sorgo, cotton, wheat and barley.

20 Claims, No Drawings

ISOXAZOLE DERIVATIVES

TECHNICAL FIELD

The present invention relates to novel isoxazole derivatives and herbicides containing them. More specifically, it relates to novel isoxazole derivatives which can selectively control a broad range of upland weeds such as grass weeds and broad-leaved weeds without causing phytotoxicity on corn, sorgo, cotton, wheat and barley, and herbicides containing them as active ingredients.

TECHNICAL BACKGROUND

During the planting time of corn, triazine-containing herbicides such as atrazine and chloroacetoanilide-containing herbicides such as alachlor and metolachlor have been conventionally used. However, atrazine shows low efficacy to grass weeds, and on the other hand, alachlor and metolachlor show low efficacy to broad-leaved weeds. It is therefore difficult at present to control grass weeds and broad-leaved weeds together simultaneously with a single herbicide. Further, even a mixture of these herbicides produces no sufficient herbicidal efficacy, and these herbicides are undesirable in view of an environmental problem due to their high dosage requirement.

On the other hand, during the planting time of cotton, trifluralin, a dinitroaniline-based herbicide, fluometuron, a urea-based herbicide and norflurazon, a pyridazine-containing herbicide have been used as herbicides for pre-emergence treatment. Further, during the planting time of wheat or barley, urea-containing herbicides such as isoproturon and chlorotoruron have been used for controlling grass weeds in particular. Since, however, these herbicides require highdosages for sufficient herbicidal efficacy, these are also environmentally undesirable.

It is known that specific isoxazole derivatives have herbicidal activity (JP-A-5-255284, WO94/18179).

Compound 2 disclosed in WO94/18179, a typical example of the isoxazole derivatives disclosed in the above publications, has the following structural formula.

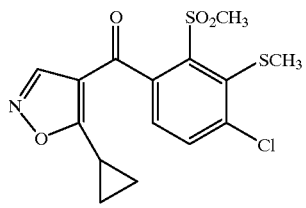

Further, a herbicidally active compound having a thiochroman ring is already known as a pyrazole derivative in which a thiochroman ring and a pyrazole ring are bonded to each other, and International Laid-open Patent Publication WO93/18031 of PCT application filed by Applicant discloses, for example, a compound (Compound No. 68) of the following formula.

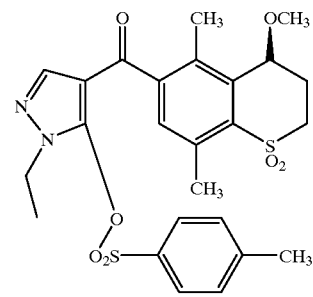

Further, there has been published the following laid-open publication including herbicide compositions having structures closer to the isoxazole derivatives of the present invention. That is, EP95/0636622A1 (JP-A-7-149742) discloses isoxazole derivatives having a structure in which isoxazole and a benzo-condensation type dicyclic group bond to each other and having herbicidal activity, and it describes a thiochroman ring which is part of the skeleton of the compounds of the present invention. However, the above publication describes no specific "Example" concerning a compound having a thiochroman ring. The above publication in Examples discloses compounds having a benzo-condensation type dicyclic group structurally similar to a thiochroman ring, for example, a compound (Compound No. 25) of the following formula. However, these compounds are practically insufficient in efficacy as herbicides.

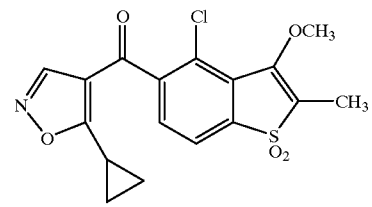

DISCLOSURE OF THE INVENTION

It is therefore a first object of the present invention to provide a novel isoxazole derivative which causes no phytotoxicity on useful crops such as corn, sorgo, cotton, wheat and barley but can selectively simultaneously control grass weeds and broad-leaved weeds as a single herbicide at a low dosage.

It is a second object of the present invention to provide a herbicide containing the above isoxazole derivative as an active ingredient.

The present inventors have made diligent studies for achieving the above objects and have found that a novel isoxazole derivative having a specific structure having a thiochroman ring causes no phytotoxicity to useful crops such as corn, sorgo, cotton, wheat and barley and can selectively simultaneously control grass weeds and broad-leaved weeds as a single herbicide at a low dosage. On the basis of this finding, the present invention has been completed.

That is, the first object of the present invention is achieved by an isoxazole derivative of the following general formula (I) (to be sometimes referred to as "isoxazole derivative (I) of the present invention" hereinafter) and by an isoxazole derivative of the following general formula (Ia) (to be sometimes referred to as "isoxazole derivative (Ia) of the present invention" hereinafter).

General formula (I)

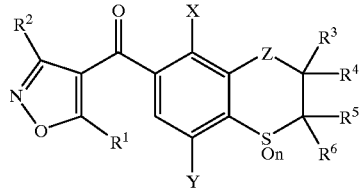

(I)

wherein $R^1$ is a $C_1$–$C_6$ alkyl group or a $C_3$–$C_6$ cycloalkyl group, $R^2$ is a hydrogen atom or a $C_1$–$C_4$ alkoxycarbonyl group, each of $R^3$ to $R^6$ is independently a hydrogen atom or a $C_1$–$C_4$ alkyl group, or $R^3$ and $R^5$ may bond to each other and form a double bond, n is an integer of 0, 1 or 2, X is a halogen atom, a $C_1$–$C_4$ haloalkyl group, a $C_1$–$C_4$ alkoxy group, a $C_1$–$C_4$ haloalkoxy group, a $C_1$–$C_4$ alkylthio group, a $C_1$–$C_4$ alkylsulfonyl group, a $C_1$–$C_4$ haloalkylthio group, a $C_1$–$C_4$ haloalkylsulfonyl group, a $C_1$–$C_4$ (di) alkylamino group, a (bis) $C_1$–$C_4$ haloalkylamino group, an amino group, a hydroxy group or a nitro group, Y is a hydrogen atom, a $C_1$–$C_4$ alkyl group, a $C_1$–$C_4$ alkoxy group or a halogen atom, and Z is a group of

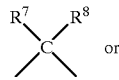

(a)

or (b)

in which each of $R^7$ and $R^8$ is independently a hydrogen atom, a $C_1$–$C_4$ alkyl group or a $C_1$–$C_4$ alkoxy group, provided that when $R^7$ and/or $R^8$ are/is $C_1$–$C_4$ alkyl group(s) or $C_1$–$C_4$ alkoxy group(s), 1 to 9 hydrogen atoms thereof may be replaced with 1 to 9 halogen atoms, further when the number of carbon atoms thereof is $C_2$–$C_4$, the substituent(s) may have unsaturated bond(s), and that when both $R^7$ and $R^8$ are $C_1$–$C_4$ alkyl groups or $C_1$–$C_4$ alkoxy groups, then $R^7$ and $R^8$ may form a 3- to 7-membered ring in which carbon atoms of the substituents bond to each other, and $R^9$ is an oxygen atom, a sulfur atom or a $C_1$–$C_4$ alkoxyimino group, provided that when $R^9$ is a $C_1$–$C_4$ alkoxyimino group, 1 to 9 hydrogen atoms thereof may be replaced with 1 to 9 halogen atoms, further when the number of carbon atoms of the substituent is $C_2$–$C_4$, the substituent may have unsaturated bond(s).

General formula (Ia)

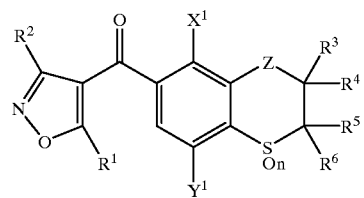

(Ia)

wherein $R^1$ to $R^6$, Z and n are as defined in the above general formula (I), $X^1$ is a halogen atom, a $C_1$–$C_4$ haloalkyl group, a $C_1$–$C_4$ alkoxy group, a $C_1$–$C_4$ haloalkoxy group, a $C_1$–$C_4$ alkylthio group, a $C_1$–$C_4$ alkylsulfonyl group or a nitro group, and $Y^1$ is a hydrogen atom, a $C_1$–$C_4$ alkyl group or a halogen atom.

Further, the second object of the present invention is achieved by a herbicide containing the isoxazole derivative of the above general formula (I) as an active ingredient (to be sometimes referred to as "herbicide (I) of the present invention" hereinafter) and by a herbicide containing the isoxazole derivative of the above general formula (Ia) as an active ingredient (to be sometimes referred to as "herbicide (Ia) of the present invention" hereinafter).

PREFERRED EMBODIMENTS OF THE INVENTION

The isoxazole derivative (I) of the present invention will be explained first.

The isoxazole derivative (I) of the present invention has the following general formula (I).

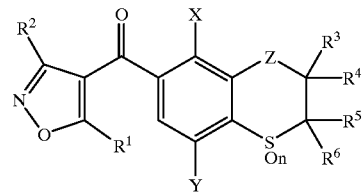

(I)

In the general formula (I) representing the isoxazole derivative (I) of the present invention, $R^1$ is a $C_1$–$C_6$ alkyl group or a $C_3$–$C_6$ cycloalkyl group. Examples of the $C_1$–$C_6$ alkyl group include methyl, ethyl, propyl, butyl, pentyl and hexyl. The propyl, butyl, pentyl and hexyl may be linear or branched. A $C_1$–$C_4$ alkyl group is preferred, methyl, ethyl or i-propyl is more preferred, and methyl is particularly preferred. Examples of the $C_3$–$C_6$ cycloalkyl group include cyclopropyl, cyclobutyl, cyclopentyl and cyclohexyl, and cyclopropyl is preferred.

$R^2$ is a hydrogen atomor a $C_1$–$C_4$ alkoxycarbonyl group. Exampless of the $C_1$–$C_4$ alkoxycarbonyl group include methoxycarbonyl, ethoxycarbonyl, propoxycarbonyl and butoxycarbonyl. The propoxycarbonyl and butoxycarbonyl may be linear or branched. $R^2$ is preferably a hydrogen atom.

Each of $R^3$, $R^4$, $R^5$ and $R^6$ is independently a hydrogen atom or a $C_1$–$C_4$ alkyl group. The $C_1$–$C_4$ alkyl group includes methyl, ethyl, propyl and butyl. The propyl and butyl may be linear or branched. A hydrogen atom or methyl is preferred. Further, $R^3$ and $R^5$ may bond to each other to form a thiochromen ring in which carbon atoms on the 2- and 3-positions of the thiochroman ring form a double bond.

n is the number of oxygen atom(s) bonding to the sulfur atom, and it is an integer of 0, 1 or 2. When n=0, a sulfide is represented. When n=1, a sulfoxide is represented. When n=2, a sulfone is represented. Preferably, n=2 (sulfone) or n=0 (sulfide).

X is a halogen atom or a $C_1$–$C_4$ haloalkyl group, a $C_1$–$C_4$ alkoxy group, a $C_1$–$C_4$ haloalkoxy group, a $C_1$–$C_4$ alkylthio group, a $C_1$–$C_4$ alkylsulfonyl group, a $C_1$–$C_4$ haloalkylthio group, a $C_1$–$C_4$ haloalkylsulfonyl group, a $C_1$–$C_4$ (di) alkylamino group, a (bis)$C_1$–$C_4$ haloalkylamino group, an amino group, a hydrox group or a nitro group.

Examples of the halogen atom as X include fluorine, chlorine, bromine and iodine. A chlorine atom is preferred.

Examples of the $C_1$–$C_4$ haloalkyl group include —$CH_2F$, —$CHF_2$, —$CF_3$, —$CH_2Cl$, —$CCl_3$, —$CH_2Br$, —$CH_2I$, —$CH_2CH_2F$, —$CH_2CF_3$, —$CF_2CH_3$, —$C_2F_5$, —$CH_2CH_2Cl$, —$CH_2CCl_3$, —$CCl_2CH_3$, —$C_2Cl_5$, —$CF(CH_3)_2$, —$CH(CF_3)CH_3$, —$CH(CF_3)_2$, —$CCl(CH_3)_2$, —$CH(CCl_3)_2$, —$CH_2CH_2CH_2F$, —$CH_2CH_2CF_3$, —$C_3F_7$, —$CH_2CH_2CH_2Cl$, —$CHClCH_2CH_3$, —$CH_2CH_2CH_2CH_2F$, —$CH_2CH_2CH_2CH_2Cl$, —$CH(CH_3)CH_2CH_2Cl$, —$CH(CF_3)C_2H_5$, —$CF(CH_3)C_2H_5$ and —$C_4F_9$. Preferred is —$CHF_2$ or —$CF_3$.

Examples of the $C_1$–$C_4$ alkoxy group include methoxy, ethoxy, propoxy and butoxy. The alkyl chain of each of the propoxy and the butoxy may be linear or branched. Methoxy is preferred.

Examples of the $C_1$–$C_4$ haloalkoxy group include —$OCH_2F$, —$OCHF_2$, —$OCF_3$, —$OCH_2Cl$, —$OCCl_3$, —$OCH_2Br$, —$OCH_2I$, —$OCH_2CH_2F$, —$OCH_2CF_3$, —$OCF_2CH_3$, —$OC_2F_5$, —$OCH_2CH_2Cl$, —$OCH_2CCl_3$, —$OCCl_2CH_3$, —$OC_2Cl_5$, —$OCF(CH_3)_2$, —$OCH(CF_3)CH_3$, —$OCH(CF_3)_2$, —$OCCl(CH_3)_2$, —$OCH(CCl_3)_2$, —$OCH_2CH_2CH_2F$, —$OCH_2CH_2CF_3$, —$OC_3F_7$, —$OCH_2CH_2CH_2Cl$, —$OCHClCH_2CH_3$, —$OCH_2CH_2CH_2CH_2F$, —$OCH_2CH_2CH_2CH_2Cl$, —$OCH(CH_3)CH_2CH_2Cl$, —$OCH(CF_3)C_2H_5$, —$OCF(CH_3)C_2H_5$ and —$OC_4F_9$. Preferred is —$OCHF_2$ or —$OCF_3$.

Examples of the $C_1$–$C_4$ alkylthio group include methylthio, ethylthio, propylthio and butylthio. The alkyl chain of each of the propylthio and the butylthio may be linear or branched. Methylthio or ethylthio is preferred.

Examples of the $C_1$–$C_4$ alkylsulfonyl group include methylsulfonyl, ethylsulfonyl, propylsulfonyl and butylsulfonyl. The alkyl chain of each of the propylsulfonyl and the butylsulfonyl may be linear or branched. Preferred is methylsulfonyl or ethylsulfonyl.

Examples of the $C_1$–$C_4$ haloalkylthio group include —$SCHF_2$, —$SCF_3$, —$SCHCl_2$, —$SCCl_3$, —$SCH_2CH_2F$, —$SCH_2CF_3$, —$SC_2F_5$, —$SCF_2CF_2H$, —$SCH(CF_3)_2$ and $SC_4F_9$. Preferred is —$SCHF_2$ or —$SCF_3$.

Examples of the $C_1$–$C_4$ haloalkylsulfonyl group include —$SO_2CHF_2$, —$SO_2CF_3$, —$SO_2CHCl_2$, —$SO_2CCl_3$, —$SO_2CH_2CH_2F$, —$SO_2CH_2CF_3$, —$SO_2C_2F_5$, —$SO_2CF_2CF_2H$, —$SO_2CH(CF_3)_2$ and $SO_2C_4F_9$. Preferred is —$SO_2CHF_2$ or —$SO_2CF_3$.

Examples of the (di)alkylamino group refers to a $C_1$–$C_4$ monoalkylamino group or a $C_1$–$C_4$ dialkylamino group, and examples thereof include methylamino, ethylamino, propylamino, butylamino, dimethylamino, diethylamino, ethyl(methyl)amino, methyl(propyl)amino and butyl(methyl) amino. In the (di)alkylamino group, the propyl group or butyl group may be linear or branched. Preferred is methylamino or dimethylamino.

The (bis)haloalkylamino group refers to a mono $C_1$–$C_4$ monohaloalkylamino group or a (bis)$C_1$–$C_4$ haloalkylamino group, and examples thereof include —$NHCHF_2$, —$NHCF_3$, —$NHCHCl_2$, —$NHCCl_3$, —$NHCH_2CH_2F$, —$NHCH_2CF_3$, —$NHC_2F_5$, —$NHCF_2CF_2H$, —$NHCH(CF_3)_2$, —$NHC_4F_9$, —$N(CHF_2)_2$, —$N(CF_3)_2$ and —$(CCl_3)_2$. Preferred is —$NHCHF_2$, —$NHCF_3$, $N(CHF_2)_3$ or —$N(CF_3)_2$.

X is particularly preferably a chlorine atom, —$CHF_2$, —$CF_3$, —$OCF_3$, —$OCH_3$, —$OCHF_2$, —$SCHF_2$, —$SCF_3$, —$SO_2CF_3$, —$N(CH_3)_2$ or nitro.

Y is a hydrogen atom, a $C_1$–$C_4$ alkyl group, a $C_1$–$C_4$ alkoxy group or a halogen atom. Examples of the $C_1$–$C_4$ alkyl group include those specified with regard to the above $R^3$, $R^4$, $R^5$ and $R^6$. Examples of the $C_1$–$C_4$ alkoxy group and the halogen atom include those specified with regard to the above X. Y is preferably a hydrogen atom, methyl, a fluorine atom or a chlorine atom, particularly preferably methyl or hydrogen.

Z is a group of

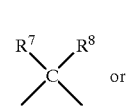 (a)

or

 (b)

In the above formula (a), each of $R^7$ and $R^8$ is independently a hydrogen atom, a $C_1$–$C_4$ alkyl group or a $C_1$–$C_4$ alkoxy group.

Examples of the $C_1$–$C_4$ alkyl group include those specified with regard to the above $R^3$, $R^4$, $R^5$ and $R^6$. When $R^7$ and/or $R^8$ are/is $C_1$–$C_4$ alkyl group(s), 1 to 9 hydrogen atoms of the carbon chain may be replaced with 1 to 9 halogen atoms. Specific examples of the halogen-substituted alkyl group include those specified with regard to the $C_1$–$C_4$ haloalkyl group included in the definition of the above X. The halogen-substituted alkyl group is more preferably —$CHF_2$, —$CF_3$, —$CCl_3$, —$CH_2CH_2F$, —$CH_2CF_3$, —$C_2F_5$ or —$CF(CH_3)_2$.

When $R^7$ and/or $R^8$ are/is $C_2$–$C_4$ alkyl group(s), carbon atoms adjacent to each other in the substituent may form unsaturated bond(s) such as double bond or triple bond. Specific examples thereof include —CH=$CH_2$, —C≡CH, —C($CH_3$)=$CH_2$, —CH=C($CH_3$)$_2$, —$CH_2$CH=$CH_2$, —CH($CH_3$)CH=$CH_2$ and —$CH_2$C≡CH. Preferred is —CH=$CH_2$, —C≡CH or —C($CH_3$)=$CH_2$.

Further, when each of $R^7$ and $R^8$ is independently a $C_1$–$C_4$ alkyl group, any carbon atom of $R^7$ and any carbon atom of $R^8$ may bond to each other and form a 3 to 7-membered ring. Specific examples thereof include

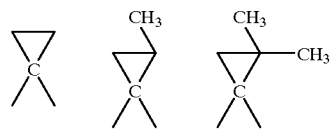

-continued

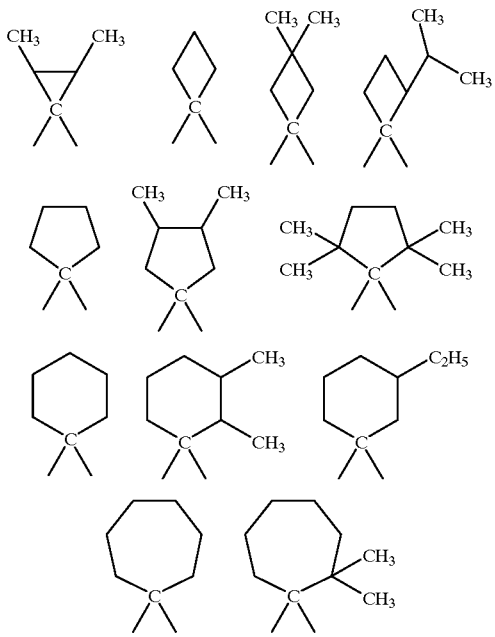

and preferred is

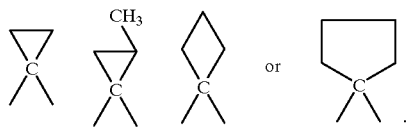

Examples of the $C_1$–$C_4$ alkoxy group include those specified with regard to the $C_1$–$C_4$ alkoxy group included in the definition of the above X. When $R^7$ and/or $R^8$ are/is $C_1$–$C_4$ alkoxy group(s), 1 to 9 hydrogen atoms of the carbon chain may be replaced with 1 to 9 halogen atoms. Specific examples of the halogen-substituted alkoxy group include those specified with regard to the $C_1$–$C_4$ haloalkoxy group included in the definition of the above X, and —$OCH_2CH_2F$ is more preferred.

When $R^7$ and/or $R^8$ are/is a $C_2$–$C_4$ alkoxy group(s), carbon atoms adjacent to each other in the substituent may form unsaturated bond(s) such as a double bond or a triple bond. Specific examples thereof include —$OCH=CH_2$, —$OC(CH_3)=CH_2$, —$OCH=C(CH_3)_2$, —$OCH_2CH=CH_2$, —$OCH_2C(CH_3)=CH_2$, —$OCH(CH_3)CH=CH_2$ and —$OCH_2C\equiv CH$. Preferred is —$OCH_2CH=CH_2$ or —$OCH_2C\equiv CH$.

Further, when each of $R^7$ and $R^8$ is independently a $C_1$–$C_4$ alkoxy group, any carbon atom of $R^7$ and any carbon atom of $R^8$ may bond to each other and form a 5 to 7-membered ring. Specific examples thereof include

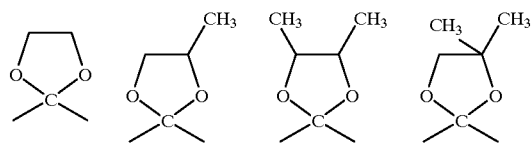

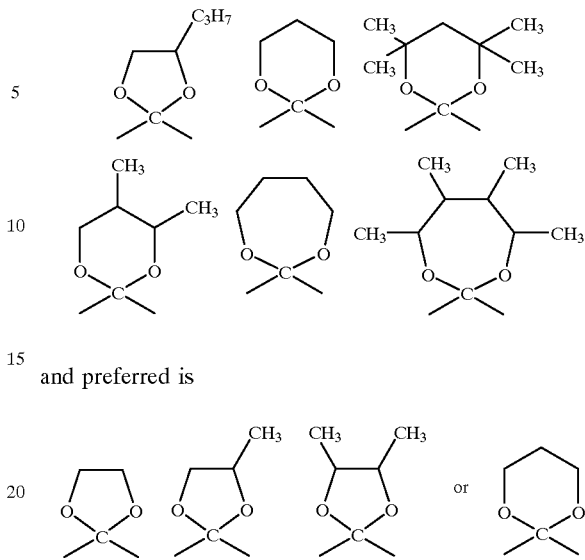

and preferred is

When Z is a group of (a), $R^7$ and $R^8$ are preferably as follows.

(i) $R^8$ is a hydrogen atom, and $R^7$ is any one of methyl, ethyl, isopropyl, —$CF_3$, —$C_2F_5$, —$CF(CH_3)_2$, —$CH=CH_2$, —$C(CH_3)=CH_2$, methoxy, ethoxy, isopropoxy, —$OCH_2CH_2F$, —$OCH_2CH=CH_2$ and —$OCH_2C\equiv CH$.

(ii) $R^7$ and $R^8$ are the same substituents, i.e., $R^7$ and $R^8$ are concurrently methyl, —$CF_3$ or methoxy.

(iii) A cyclopropane ring, a cyclobutane ring, a cyclopentane ring or 2,5-dioxolan ring in which identical $R^7$ and $R^8$ bond, each of said rings including a carbon atom on the 4-position of the thiochroman ring.

In the group (b) in the cdefinition of Z, $R^9$ is an oxygen atom, a sulfur atom or a $C_1$–$C_4$ alkoxyimino group. Examples of the $C_1$–$C_4$ alkoxyimino group include methoxyimino, ethoxyimino, propoxyimino and butoxyimino. The alkyl chain of each of the propoxyimino and the butoxyimino may be linear or branched. When $R^9$ is a $C_1$–$C_4$ alkoxyimino group, 1 to 9 hydrogen atoms of the carbon chain may be replaced with 1 to 9 halogen atoms. Specific examples thereof include =$NOCH_2CH_2F$, =$NOCH_2CH_2Cl$, =$NOCH_2CH_2Br$, =$NOCH_2CH_2I$, =$NOCH_2CF_3$, =$NOCH_2CCl_3$, =$NOCF(CH_3)_2$, =$NOCH(CF_3)CH_3$, =$NOCH(CF_3)_2$, =$NOCH(CCl_3)_2$, =$NOCH_2CH_2CH_2F$, =$NOCH_2CH_2CF_3$, =$NOCH_2CF_2CF_3$, =$NOCH_2CH_2CH_2Cl$, =$NOCH_2CH_2CH_2CH_2F$, =$NOCH_2CH_2CH_2CH_2Cl$, =$NOCH(CH_3)CH_2CH_2Cl$ and =$NOCH(CF_3)C_2H_5$. Preferred is =$NOCH_2CH_2F$, =$NOCH_2CH_2Cl$, =$NOCF(CH_3)_2$ and =$NOCH(CF_3)CH_3$.

When $R^9$ is a $C_2$–$C_4$ alkoxyimino group, carbon atoms adjacent to each other in the substituent may form unsaturated bond(s) such as a double bond or a triple bond. Specific examples thereof include =$NOCH=CH_2$, =$NOC(CH_3)=CH_2$, =$NOCH=C(CH_3)_2$, =$NOCH_2CH=CH_2$, =$NOCH_2C(CH_3)=CH_2$, =$NOCH=(CH_3)CH=CH_2$ and =$NOCH_2C\equiv CH$. Preferred is =$NOCH_2CH=CH_2$ or =$NOCH_2C\equiv CH$.

When Z is the group (b), preferably, $R^9$ is an oxygen atom, methoxyimino, ethoxyimino, =$NOCH_2CH_2F$, =$NOCH_2CH=CH_2$ or =$NOCH_2C\equiv CH$, and particularly preferably, $R^9$ is methoxyimino.

The isoxazole derivative (I) of the present invention includes a compound of the general formula (Ib) as a preferred embodiment.

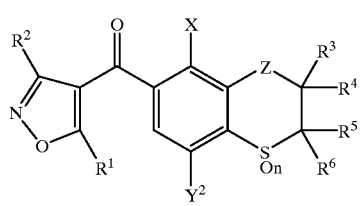

(Ib)

In the general formula (Ib), $R^1$, $R^2$, $R^3$, $R^4$, $R^5$, $R^6$, n, X and Z are as explained with regard to the above general formula (I).

In the general formula (Ib), $Y^2$ is a $C_1$–$C_4$ alkyl group, a $C_1$–$C_4$ alkoxy group or a halogen atom. The $C_1$–$C_4$ alkyl group, the $C_1$–$C_4$ alkoxy group and the halogen atom are as explained with regard to Y in the above general formula (I).

The isoxazole derivative (I) of the present invention includes a compound of the general formula (Id) as another preferred embodiment.

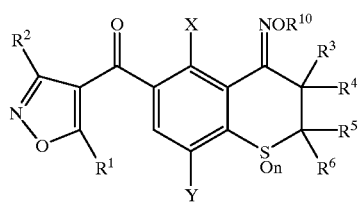

(Id)

In the general formula (Id), $R^1$, $R^2$, $R^3$, $R^4$, $R^5$, $R^6$, n, X and Y are as explained with regard to the above general formula (I).

In the general formula (Id), the group corresponding to Z in the general formula (I) is

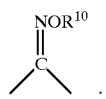

$R^{10}$ is a $C_1$–$C_4$ alkyl group, and the $C_1$–$C_4$ alkyl group is as explained with regard to X in the above general formula (I). Further, $R^{10}$ may be a substituent in which 1 to 9 hydrogen atoms of the $C_1$–$C_4$ alkyl group are replaced with 1 to 9 halogen atoms. When $R^{10}$ is a $C_2$–$C_4$ alkyl group, the $C_2$–$C_4$ alkyl group may have unsaturated bond(s). Specific examples of $R^{10}$ in this case include those explained with regard to $R^7$ and $R^8$ in the above general formula (I).

The isoxazole derivative of the above general formula (Id) has remarkably excellent herbicidal efficacy over the compound of the general formula (I) in which Z is other than the above alkoxyimino group, for example, Z is

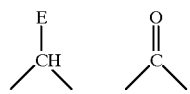

in which E is a $C_1$–$C_4$ alkoxy group or haloalkoxy group, as will be shown in Herbicide Examples to be described later.

The isoxazole derivative (Ia) of the present invention will be explained hereinafter.

The isoxazole derivative (Ia) of the present invention has the general formula (Ia).

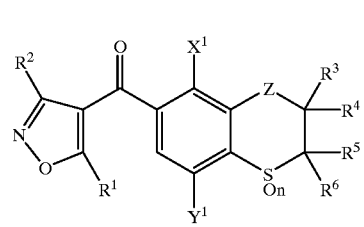

(Ia)

The compound of the above general formula (Ia) is one embodiment of the isoxazole derivative of the general formula (I), and $R^1$ to $R^6$, Z and n are as explained with regard to the general formula (I).

$X^1$ is a halogen atom, a $C_1$–$C_4$ haloalkyl group, a $C_1$–$C_4$ alkoxy group, a $C_1$–$C_4$ haloalkoxy group, $C_1$–$C_4$ alkylthio group, a $C_1$–$C_4$ alkylsulfonyl group or a nitro group.

The halogen atom, the $C_1$–$C_4$ haloalkyl group, the $C_1$–$C_4$ alkoxy group, the $C_1$–$C_4$ haloalkoxy group, the $C_1$–$C_4$ alkylthio group and the $C_1$–$C_4$ alkylsulfonyl group included in the definition of $X^1$ include those explained with regard to X in the general formula (I).

$X^1$ is particularly preferably a chlorine atom, —$CHF_2$, —$CF_3$, —$OCF_3$, —$OCH_3$, —$OCHF_2$ or a nitro group.

$Y^1$ is a hydrogen atom, a $C_1$–$C_4$ alkyl group or a halogen atom. The $C_1$–$C_4$ alkyl group includes those specified with regard to $R^3$, $R^4$, $R^5$ and $R^6$ in the general formula (I). The halogen atom includes those specified with regard to X in the general formula (I). $Y^1$ is preferably a hydrogen atom, methyl, a fluorine atom or a chlorine atom, particularly preferably methyl or a hydrogen atom.

The isoxazole derivative (Ia) of the present invention includes a compound of the general formula (Ic) as a preferred embodiment.

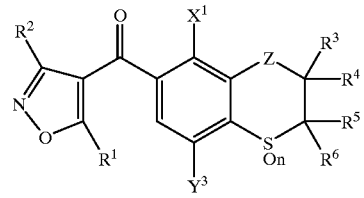

(Ic)

In the general formula (Ic), $R^1$, $R^2$, $R^3$, $R^4$, $R^5$, $R^6$, n, $X^1$ and Z are as explained with regard to the general formula (Ia).

In the general formula (Ic), $Y^3$ is a $C_1$–$C_4$ alkyl group or a halogen atom. The $C_1$–$C_4$ alkyl group and the halogen atom include those specified with regard to $Y^1$ in the general formula (Ia).

The isoxazole derivative (Ia) of the present invention includes a compound of the general formula (Ie) as another preferred embodiment.

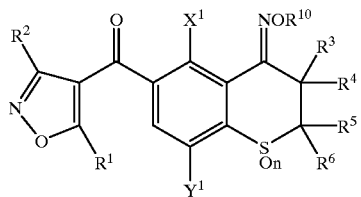
(Ie)

In the general formula (Ie), $R^1$, $R^2$, $R^3$, $R^4$, $R^5$, $R^6$, n, $X^1$ and $Y^1$ are as explained with regard to the general formula (Ia).

$R^{10}$ is as explained with regard to the general formula (Id).

The isoxazole derivative of the above general formula (Ie) has remarkably excellent herbicidal efficacy over the compound of the general formula (Ia) in which Z is other than the above alkoxyimino group, for example, Z is

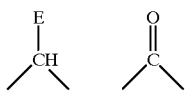

in which E is a $C_1$–$C_4$ alkoxy group or haloalkoxy group, as will be shown in Herbicide Examples to be described later.

Isomers of the isoxazole derivative (I) of the present invention, represented by the general formula (I), and the process for the production of the isoxazole derivative (I) of the present invention will be explained hereinafter. The isoxazole derivative (Ia) of the present invention is included in the following explanation, since it is one embodiment of the above isoxazole derivative (I).

The isoxazole derivative of the general formula (I)

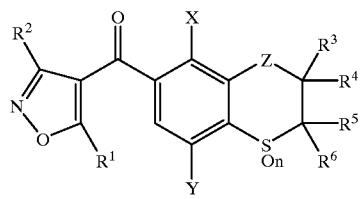
(I)

may contain asymmetric carbons, and may include various isomers, depending upon kinds of the substituents $R^3$, $R^4$, $R^5$ and $R^6$. The isoxazole derivative of the present invention includes all the isomers and mixtures of these.

The isoxazole derivative of the general formula (I) in which Z is the group (a), i.e., an isoxazole derivative of the general formula (If),

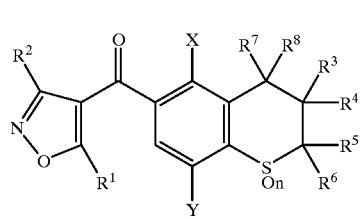
(If)

may contain asymmetric carbon, and may include various isomers, depending upon kinds of the substituents $R^7$ and $R^8$, and the isoxazole derivative of the present invention includes all the isomers and mixtures of these.

The isoxazole derivative of the general formula (I) in which Z is the group (b) and $R^9$ is a $C_1$–$C_4$ alkoxyimino group, i.e., the isoxazole derivative of the general formula (Id)

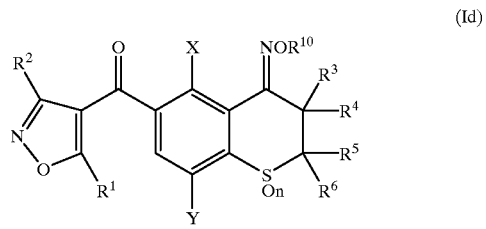
(Id)

includes geometrical isomers of the following general formulae (Id1) and (Id2) as shown below, and the isoxazole derivative of the present invention includes any one of these and a mixture of these.

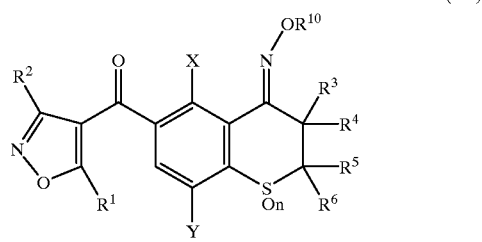
(Id1)

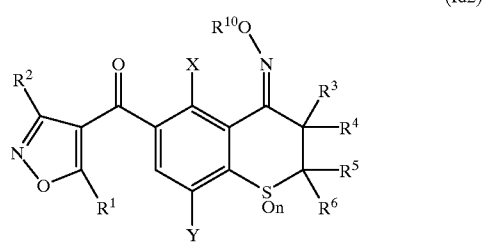
(Id2)

The novel isoxazole derivative of the present invention can be produced according to known methods described in JP-A-3-118374 and JP-A-6-271554. For example, it can be produced according to the following reaction scheme.

The process for the production of the compound of the general formula (I) in which $R^2$ is a hydrogen atom, i.e., a compound of the general formula (Ig), will be explained in detail below.

Reaction scheme 1

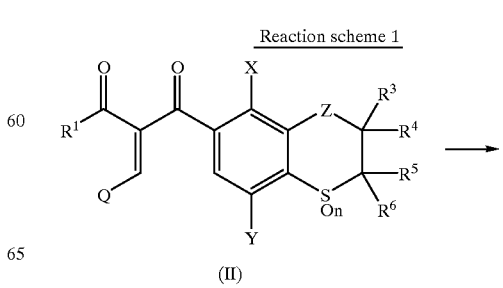
(II)

-continued

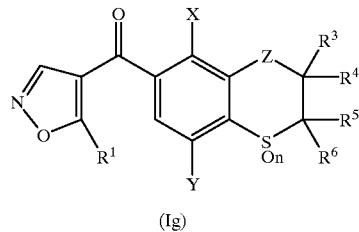

(Ig)

wherein $R^1$, $R^3$, $R^4$, $R^5$, $R^6$, X, Y, Z and n are as defined in the general formula (I), and Q is a $C_1$–$C_4$ alkoxy group or a $C_1$–$C_4$ dialkylamino group.

The above reaction scheme 1 shows the production of an isoxazole derivative of the general formula (Ig), provided by the present invention, by a method in which 2-dialkylaminomethylidene derivative of the general formula (II) (in which Q is dialkylamino) or 2-alkoxymethylidene derivative of the general formula (II) (in which Q is alkoxy) is reacted with a hydroxyamine salt in a solvent such as ethanol or acetonitrile optionally in the presence of a base such as triethylamine or sodium acetate at a temperature in the range of from room temperature to the reflux temperature of the solvent. The isoxazole derivative of the above general formula (Ig) is limited to the isoxazole derivative of the general formula (I) in which $R^2$ is hydrogen.

After the completion of the reaction, according to a conventional method, the isoxazole derivative of the present invention synthesized by the above method, is isolated by distilling off the solvent, dissolving the residue in a solvent such as methylene chloride, washing the resultant solution with water, drying the organic layer over a dehydrating agent such as anhydrous sodium sulfate and distilling off the solvent under reduced pressure. Further, the so-obtained residue may be purified by means such as flash column chromatography (silica gel; Wakogel C300 (trade name); hexane/ethyl acetate =2:1).

The 2-dialkylaminomethylidene derivative or the 2-alkoxymethylidene derivative as a starting material in the reaction scheme 1 can be prepared according to the reaction scheme 2

Reaction scheme 2

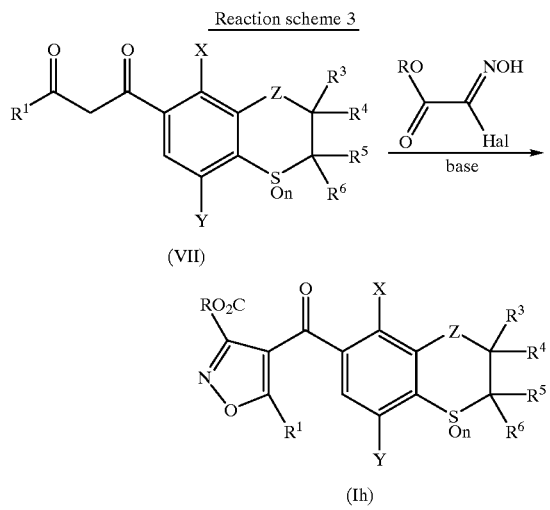

wherein $R^1$, $R^3$, $R^4$, $R^5$, $R^6$, X, Y, Z and n are as defined in the general formula (I) and Q is a $C_1$–$C_4$ alkoxyl group or a $C_1$–$C_4$ dialkylamino group.

The above reaction scheme 2 shows the production of 2-alkoxymethylidene derivative (II) (in which Q is alkoxy) by a method in which a 1,3-diketone derivative of the general formula (VII) is reacted with an orthoester such as triethyl orthoformate in the presence of an acid catalyst such as acetic anhydride at the reflux temperature of a reaction mixture or the production of 2-dimethylaminomethylidene (II) (in which Q is dialkylamino) by a method in which 1,3-diketone derivative of the general formula (VII) is reacted with an amideacetal such as N,N-dimethylformamidedimethylacetal in an inert solvent such as dioxane at a temperature in the range of from room temperature to the reflux temperature of the solvent. The so-obtained 2-alkoxymethylidene derivative (II) or 2-dimethylaminomethylidene derivative (II) can be used for the synthesis of the isoxazole derivative without their purification.

The method of producing the isoxazole derivative of the general formula (I) in which $R^2$ is $C_1$–$C_4$ alkoxycarbonyl, i.e., an isoxazole derivative of the general formula (Ih), will be explained below.

Reaction scheme 3 wherein $R^1$, $R^3$, $R^4$, $R^5$, $R^6$, X, Y, Z and n are as defined in the general formula (I), R is a $C_1$–$C_4$ alkyl group and Hal is a halogen atom.

The above reaction scheme 3 shows the production of the isoxazole derivative of the general formula (Ih), provided by the present invention, by a method in which 1,3-diketone derivative of the general formula (VII) is reacted with a compound represented by $RO_2CC(Hal)=NOH$ in an inert solvent such as dichloromethane or acetonitrile in the presence of a base such as triethylamine at a temperature in the range of from room temperature to the reflux temperature of a reaction mixture. The isoxazole derivative of the above general formula (Ih) is limited to the isoxazole derivative of the general formula (I) in which $R^2$ is a $C_1$–$C_4$ alkoxycarbonyl group.

The 1,3-diketone derivative of the general formula (VII) as a starting material in the reaction scheme 3 can be produced according to Reaction scheme 4 or 5.

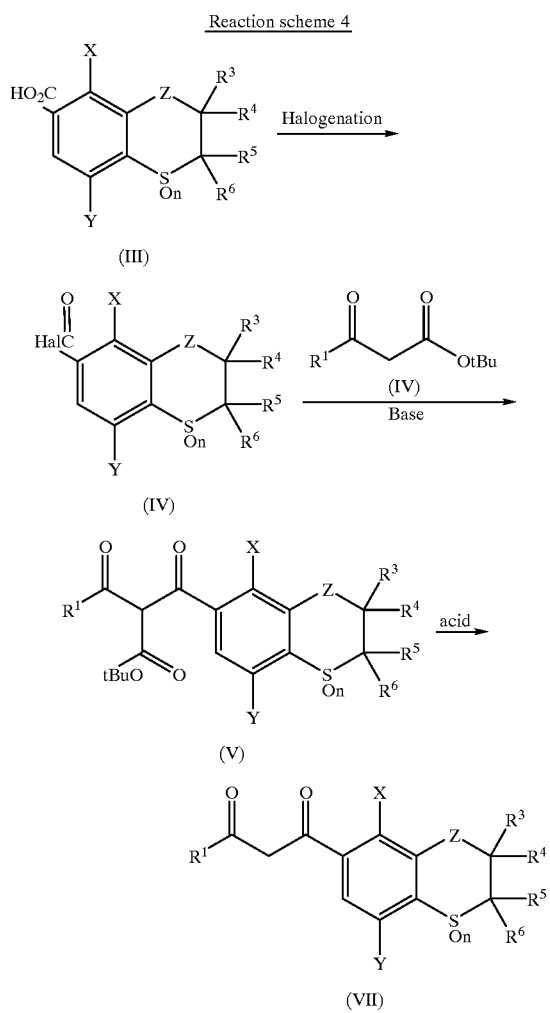

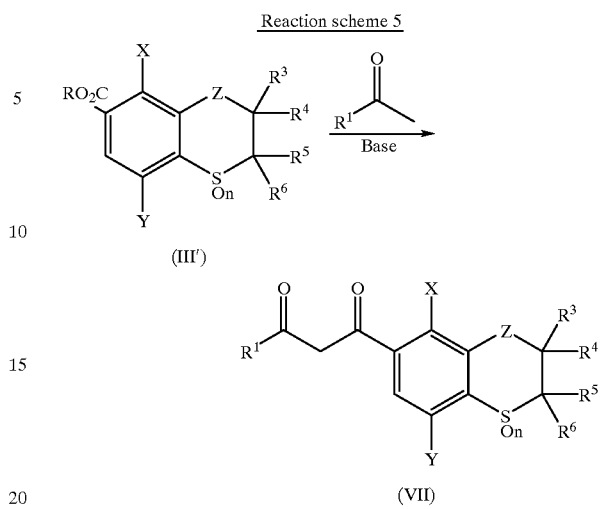

wherein $R^1$, $R^3$, $R^4$, $R^5$, $R^6$, X, Y, Z and n are as defined in the general formula (I), and Hal is a halogen atom.

The above reaction scheme 4 shows the production of the 1,3-diketone derivative of the general formula (VII) by a method including a first step of reacting a carboxylic acid of the general formula (III) with a halogenating agent such as thionyl chloride, oxalyl chloride or phosphorus oxychloride to form acyl halide of the general formula (IV), a second step of reacting the acyl halide of the general formula (IV) with tert-butylacylacetate of the general formula (VI) in an inert solvent such as tetrahydrofuran or diethyl ether in the presence of a base such as sodium methoxide or magnesium ethoxide at a temperature in the range of from room temperature to the reflux temperature of the solvent, to form a tert-butyldiketoacetate of the general formula (V), and a third step of decarboxylating the tert-butyldiketoacetate of the general formula (V) in the presence of an acid catalyst such as 4-toluenesulfonic acid.

wherein $R^1$, $R^3$, $R^4$, $R^5$, $R^6$, X, Y, Z and n are as defined in the general formula (I) and R is a $C_1$–$C_4$ alkyl group.

The above reaction scheme 5 shows the production of 1,3-diketone derivative of the general formula (VII) by a method in which carboxylic acid ester derivative of the general formula (III') is reacted with $R^1COCH_3$ in an ether solvent such as tetrahydrofuran or diethyl ether in the presence of a base such as sodium hydride or sodium tert-butoxide at a temperature in the range of from 0° C. to the reflux temperature of a reaction mixture.

The carboxylic acid ester derivative of the general formula (III') can be produced, for example, by reacting a corresponding carboxylic acid of the general formula (III) with an alcohol represented by ROH (in which R is a $C_1$–$C_4$ alkyl group) in the presence of a dehydrating agent such as sulfuric acid at a temperature in the range of from room temperature to the reflux temperature of a reaction mixture according to the following Reaction scheme 6.

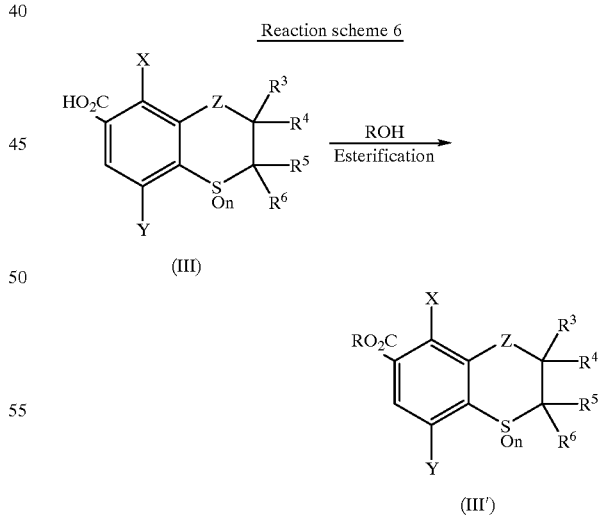

wherein $R^3$, $R^4$, $R^5$, $R^6$, X, Y, Z and n are as defined in the general formula (I) and R is a $C_1$–$C_4$ alkyl group.

The carboxylic acid derivative of the general formula (III) (and its carboxylic acid ester derivative of the general formula (III')) can be produced by a variety of methods disclosed, e.g., in International Laid-open Publication WO96/25413.

The herbicide (I) of the present invention contains, as an active ingredient, the isoxazole derivative (I) of the general formula (I) provided by the present invention. The herbicide (Ia) of the present invention contains, as an active ingredient, the isoxazole derivative (Ia) of the general formula (Ia) provided by the present invention. The isoxazole derivative of the present invention is mixed with a liquid carrier such as a solvent or a solid carrier such as a mineral fine powder, and the mixture can be prepared into the form of a wettable powder, an emulsifiable concentrate, a dust, granules, or the like. For imparting the preparation with emulsifiability, dispersibility and spreadability, a surfactant can be added.

When the herbicide of the present invention is used in the form of a wettable powder, generally, a composition is prepared by mixing 10 to 55% by weight of the isoxazole derivative of the present invention, 40 to 88%, by weight of a solid carrier and 2 to 5% by weight of a surfactant, and the composition can be used as a wettable powder. Further, when it is used in the form of an emulsifiable concentrate, generally, it can be prepared by mixing 20 to 50% by weight of the isoxazole derivative of the present invention, 35 to 75% by weight of a solvent and 5 to 15% by weight of a surfactant.

On the other hand, when herbicide of the present invention is used in the form of a dust, generally, it can be prepared by mixing 1 to 15% by weight of the isoxazole derivative of the present invention, 80 to 97% by weight of a solid carrier and a 2 to 5% by weight of a surfactant. Further, when it is used in the form of granules, it can be prepared by mixing 1 to 15% by weight of the isoxazole derivative of the present invention, 80 to 97% by weight of a solid carrier and 2 to 5% by weight of a surfactant. The above solid carrier can be selected from mineral fine powders, and the mineral fine powders include oxides such as diatomaceous earth and slaked lime, phosphates such as apatite, sulfates such as gypsum, and silicates such as talc, pyroferrite, clay, kaolin, bentonite, acid clay, white carbon, powdered quartz and powdered silica.

The solvent is selected from organic solvents. Specific examples of the solvent include aromatic hydrocarbons such as benzene, toluene and xylene, chlorinated hydrocarbons such as o-chlorotoluene, trichloroethane and trichloroethylene, alcohols such as cyclohexanol, amyl alcohol and ethylene glycol, ketones such as isophorone, cyclohexanone and cyclohexenyl-cyclohexanone, ethers such as butyl cellosolve, diethyl ether and methyl ethyl ether, esters such as isopropyl acetate, benzyl acetate and methyl phthalate, amides such as dimethylformamide, and mixtures of these.

Further, the surfactant can be selected from anionic, nonionic, cationic and amphoteric ones (amino acid and betaine).

The herbicide of the present invention may contain, as active ingredients, other herbicidally active component in combination with the isoxazole derivative of (I) or (Ia) represented by the general formula (I) or (Ia) as required. The "other" herbicidally active component can be selected from phenoxy-, diphenyl ether-, triazine-, urea-, carbamate-, thiocarbamate-, acid anilide-, pyrazole-, phosphoric acid-, sulfonylurea- and oxadiazone-based herbicides as required.

Further, the herbicide of the present invention may be used as a mixture with any one of insecticides, bactericides, plant growth regulators and fertilizers.

The herbicide of the present invention can be used as a herbicide for upland soil by any method of pre-emergence treatment, treatment by mixing it with soil, and post-emergence treatment. The cropland weeds to which the compound of the present invention is applied include broad-leaved weeds such as solanaceous weeds typified by black nightshade (*Solanum nigrum*) and Jimsonweed (*Datura stramonium*); malvaceous weeds typified by velvetleaf (*Abutilon theophrasti*) and pricky sida (*Sida spinosa*); convolvulaceous weeds typified by morning-glories (Empmoea spps.) such as tall morning-glory (*Ipomoea purpurea*) and hedge bindweeds (Calystegia spps.); amaranthaceous weeds typified by livid amaranth (*Amaranthus lividus*); composite weeds typified by cocklebur (*Xanthium strumarium*), common ragweed (*Ambrosia artemisiifolia*), sunflower (*Helianthus annus*), hairy galinsoga (*Galinsoga ciliata*), Canada thistle (*Cirsium arvense*), groundsel (*Senecio vulgaris*) and annual fleabane (*Erigeron annus*); brassicaceous weeds typified by yellow cress (*Rorippa indica*), wild mustard (*Sinapis arvensis*) and shepherdspurse (*Capsella bursa-pastris*); polygonaceous weeds typified by wild buckwheat (*Polygonum convolvulus*) and wild buckwheat (*Polygonum convolvulus*); portulacaceous weeds typified by common purslane (*Portulaca oleracea*); chenopodiaceous weeds typified by common lambsquaters (*Chenopodium album*), fig-leaved goosefoot (*Chenopodium ficifolium*) and kochia (*Kochia scoparia*); caryophyllaceous weeds typified by common chickweed (*Stellaria media*); scrophularaceous weeds typified by persian speedwell (*Veronica persica*); commelinaceous weeds typified by Asiatic dayflower (*Commelina communis*); labiatae weeds typified by henbit (*Laminum amplexicaule*) and purple deadnettle (*Lamium purpureum*); euphorbiaceous weeds typified by milk purslane (*Euphorbia supina*) and spotted spurge (*Euphorbia maculata*); rubiaceous weeds typified by bedstraw (*Galium spurium*), cleavers (*Galiumaparine*) and madder (*Rubia akane*); violaceous weeds typified by violet (*Viola arvensis*); and leguminous weeds typified by hemp sesbania (*Sesbania exaltata*) and sicklepod (*Cassia obtusifolia*); graminaceous weeds typified by sorghum (*Sorghum bicolor*), fall panicum (*Panicum dichotomiflorum*), Johnsongrass (*Sorghum halepense*), barnyardgrass (*Ehinocholoa crus-galli*), henry crabgrass (*Digitaria adscendens*), wildoat (*Avena fatua*), goosegrass (*Eleusine indica*), green foxtail (*Setaria viidis*) and water foxtail (*Alopecurus aequalis*); and cyperaceous weeds typified by purple nutsedge (*Cyperus rotundus, Cyperus esculentus*).

Further, the herbicide of the present invention can be also used for any one of pre-emergence treatment and post-emergence treatment under submergence as a herbicide for paddy land. Examples of paddy weeds include alismataceous weeds typified by oriental waterplantain (*Alisma canaliculatum*), arrowhead (*Sagittaria trifolia*) and Sagittaria pygmaea, cyperaceous weeds typified by umbrella plant (*Cyperus difformis*), Cyperus serotinus, bulrush (*Scirpus juncoides*) and water chestnut (*Eleochadaris kuroguwai*); scrothulariaceous weeds typified by common falsepimpernel (*Lindernia pyxidaria*); potenderiaceous weeds typified by monochoria (*Monochorha Vaginalis*); potamogetonaceous weeds typified by largeleaf pondweed (*Potamogeton distinctus*); lythraceous weeds typified by toothcup (*Rotala indica*); and graminaceous weeds typified by barnyardgrass (*Echinochloa crus-galli*).

Further, the herbicide of the present invention can be applied for controlling various weeds in sports grounds, vacant land, railroad sides, etc., in addition to upland field, paddy land and orchards.

The present invention will be specifically explained with reference to Preparation Examples and Herbicide Examples hereinafter, while the present invention shall not be limited by these Examples.

Referential Preparation Example 1

Synthesis of 3-cyclopropyl-2-(dimethylamino) methylidene-1-[5-chloro-8-fluoro-4-(2-fluoroethoxy) thiochroman-1,1-dioxide-6-yl]propane-1,3-dione 1-1) tert-butyl 3-cyclopropyl-2-[5-chloro-8-fluoro-4-(2-fluoroethoxy)thiochroman-1,1-dioxide-6-carbonyl]-3-oxonropionate 1.2 Grams (3.5 mmol) of 6-carboxyl-5-chloro-8-fluoro-4-(2-fluoroethoxy)thiochorman-1,1-dioxide was dissolved in 5 ml of dichloroethane, 0.8 ml of thionyl chloride was added, and the mixture was heated under reflux for 3 hours. After the completion of the reaction, excessive thionyl chloride and dichloroethane were distilled off under reduced pressure, and the remaining oil was dissolved in 5 ml of tetrahydrofuran (THF) to obtain a solution of acyl chloride in THF. Separately, 0.8 g (4.2 mmol) of tert-butyl 3-cyclopropyl-3-oxopropionate and 0.5 g (4.2 mmol) of magnesium diethoxide were dissolved in 5 ml of THF, and the mixture was stirred at room temperature for 2 hours. Then, to this mixture was added the previously prepared solution of a carboxylic acid halide in THF, and the resultant mixture was stirred at room temperature for 3 hours. After the completion of the reaction, the solvent was distilled off under reducedpressure, and the remaining oil was dissolved in ethyl acetate. The mixture was washed with a 5% hydrochloric acid aqueous solution and with a saturated sodium chloride aqueous solution, and dried over anhydrous sodium sulfate. The solvent was distilled off under reduced pressure to give 2.0 g (yield 100%) of tert-butyl 3-cyclopropyl-2-[5-chloro-8-fluoro-4-(2-fluoroethoxy)thiochroman-1,1-dioxide-6-carbonyl]-3-oxopropionate (Compound No. V-1).

1-2) 3-Cyclopropyl-1-[5-chloro-8-fluoro-4-(2-fluoroethoxy)thiochroman-1,1-dioxide-6-yl]propane-1,3-dione 2.0 Grams (3.9 mmol) of tert-butyl 3-cyclopropyl-2-[5-chloro-8-fluoro-4-(2-fluoroethoxy)thiochroman-1,1-dioxide-6-carbonyl]-3-oxopropionate and 0.08 g (0.4 mmol) of 4-toluenesulfonic acid were added to 10 ml of toluene, and the mixture was heated under reflux for 3 hours. The reaction mixture was cooled, and then ethyl acetate was added. The mixture was washed with a saturated sodium hydrogencarbonate aqueous solution and with a saturated sodium chloride aqueous solution, and dried over anhydrous sodium sulfate. The solvent was distilled off under reduced pressure, and the residue was purified by silica gel column chromatography (eluting solution; hexane/ethyl acetate= 3:1) to give 1.1 g (yield 72%) of 3-cyclopropyl-1-[5-chloro-8-fluoro-4-(2-fluoroethoxy)thiochroman-1,1-dioxide-6-yl] propane-1,3-dione (Compound No. VII-1.

1-3) 3-Cyclopropyl-2-(dimethylamino)methylidene-1-[5-chloro- 8-fluoro-4-(2-fluoroethoxy) thiochroman-1,1-dioxide-6-yl]propane-1,3-dione 1.0 Gram (2.25 mmol) of 3-cyclopropyl-1-[5-chloro-8-fluoro-4-(2-fluoroethoxy)thiochroman-1,1-dioxide-6-yl] propane-1,3-dione was dissolved in 5 ml of dioxane, 0.43 ml (3.2 mmol) of N,N-dimethylformamidedimethylacetal was added, and the mixture was stirred at room temperature for about 10 hours. After the completion of the reaction, the solvent was distilled off under reduced pressure to give 1.2 g of 3-cylcopropyl-2-(dimethylamino)methylidene-1-[5-chloro-8-fluoro-4-(2-fluoroethoxy)thiochroman-1,1-dioxide-6-yl]propane-1,3-dione (Compound No. II-1) as a crude product. This compound was used as a starting material in Preparation Example 1 without any further purification.

Referential Preparation Example 2

Synthesis of 3-cyclopropyl-2-(dimethylamino) methylidene-1-(5-chloro-3,3,8-trimethyl-4-oxothiochroman-1,1-dioxide-6-yl)propane-1,3-dione 2-1) tert-Butyl 3-cyclopropyl-2-(5-chloro-3,3,8-trimethyl-4-oxothiochorman-1,1-dioxide-6-carbonyl)-3-oxopripionate tert-Butyl 3-cyclopropyl-2-(5-chloro-3,3,8-trimethyl-4-oxothiochorman-1,1-dioxide-6-carbonyl)-3-oxopropionate (Compound No. V-2) was obtained at a yield of 100% in the same manner as in Referential Preparation Example 1-1 except that the 6-carboxyl-5-chloro-8-fluoro-4-(2-fluoroethoxy)thiochorman-1,1-dioxide used in Referential Preparation Example 1-1 was replaced with 6-carboxyl-5-chloro-3,3,8-trimethyl-4-oxothiochroman-1,1-dioxide.

2-2) 3-Cyclopropyl-1-(5-chloro-3,3,8-trimethyl-4-oxothiochroman- 1,1-dioxide-6-yl)propane-1,3-dione 3-Cyclopropyl-1-(5-chloro-3,3,8-trimethyl-4-oxothiochroman-1,1-dioxide-6-yl)propane-1,3-dione (Compound No. VII-2) was obtained at a yield of 80% in the same manner as Referential Preparation Example 1-2 except that the tert-butyl 3-cyclopropyl-2-[5-chloro-8-fluoro-4-(2-fluoroethoxy)thiochroman-1,1-dioxide-6-carbonyl]-3-oxopropionate used in Referential Preparation Example 1-2 was replaced with tert-butyl 3-cyclopropyl-2-(5-chloro-3,3,8-trimethyl-4-oxothiochorman-1,1-dioxide-6-carbonyl)-3-oxopripionate.

2-3) 3-Cyclopropyl-2-(dimethylamino)methylidene-1-(5-chloro-3,3,8-trimethyl-4-oxothiochroman-1,1-dioxide-6-yl)propane-1,3-dione 3-Cyclopropyl-2-(dimethylamino)methylidene-1-(5-chloro-3,3,8-trimethyl-4-oxothiochroman-1,1-dioxide-6-yl) propane-1,3-dione (Compound No. II-2) was obtained as a crude product in the same manner as in Referential Preparation Example 1-3 except that the 3-cyclopropyl-1-[5-chloro-8-fluoro-4-(2-fluoroethoxy)thiochroman-1,1-dioxide-6-yl] propane-1,3-dione used in Referential Preparation Example 1-3 was replaced with 3-cyclopropyl-1-(5-chloro-3,3,8-trimethyl-4-oxothiochroman-1,1-dioxide-6-yl)propane-1,3-dione. The above-obtained compound was used as a starting material in Preparation Example 2 without any further purification.

Referential Preparation Example 3

Synthesis of 3-cyclopropyl-2-(dimethylamino) methylidene-1-(5-chloro-8-methyl-4-methoxyiminothiochroman-1,1-dioxide-6-carbonyl) propane-1,3-dione 3-1) tert-Butyl 3-cyclopropyl-2-(5-chloro-8-methyl-4-methoxyiminothiochorman- 1,1-dioxide-6-carbonyl)-3-oxopropionate tert-Butyl 3-cyclopropyl-2-(5-chloro-8-methyl-4-methoxyiminothiochorman-1,1-dioxide-6-carbonyl)-3- oxopripionate (Compound No. V-3) was obtained at a yield of 29% in the same manner as in Referential Preparation Example 1-1 except that the 6-carboxyl-5-chloro-8-fluoro-4-(2-fluoroethoxy)thiochorman-1,1-dioxide used in Referential Preparation Example 1-1 was replaced with 6-carboxyl-5-chloro-8-methyl-4-methoxyiminothiochroman-1,1-dioxide.

3-2) 3-Cyclopropyl-1-(5-chloro-8-methyl-4-methoxyiminothiochroman-1,1-dioxide-6-yl)propane-1,3-dione 3-Cyclopropyl-1-(5-chloro-8-methyl-4-methoxyiminothiochroman-1,1-dioxide-6-yl)propane-1,3-dione (Compound No. VII-3) was obtained at a yield of 45% in the same manner as Referential Preparation Example 1-2 except that the tert-butyl 3-cyclopropyl-2-[5-chloro-8-fluoro-4-(2-fluoroethoxy)thiochrcman-1,1-dioxide-6-carbonyl]-3-oxopropionate used in Referential Preparation Example 1-2 was replaced with tert-butyl 3-cyclopropyl-2-(5-chloro-3,3,8-trimethyl-4-oxothiochorman-1,1-dioxide-6-carbonyl)-3-oxopropionate.

3-3) 3-Cycloproyyl-2-(dimethylamino)methylidene-1-(5-chloro-8-methyl-4-methoxyiminothiochroman-1,1-dioxide-6-yl)propane-1,3-dione 3-Cyclopropyl-2-(dimethylamino)methylidene-1-(5-chloro-8-methyl-4-methoxyiminothiochroman-1,1-dioxide-6-yl)propane-1,3-dione (Compound No. II-3) was obtained as a crude product in the same manner as in Referential Preparation Example 1-3 except that the 3-cyclopropyl-1-[5-chloro-8-fluoro-4-(2-fluoroethoxy)thiochroman-1,1-dioxide-6-yl] propane-1,3-dione used in Referential Preparation Example 1-3 was replaced with 3-cyclopropyl-1-(5-chloro-8-methyl-4-methoxyiminothiochroman-1,1-dioxide-6-yl)propane-1,3-dione. The above-obtained compound was used as a starting material in Preparation Example 3 without any further purification.

Table 1 shows the structural formulae of Compounds Nos. V-1, V-2 and V-3. Table 2 shows the structural formulae and NMR data of Compounds Nos. VII-1, VII-2 and VII-3. Table 3 shows the structural formulae of Compounds Nos. II-1, II-2 and II-3.

Referential Preparation Examples 4–11
Synthesis of 3-cyclopropyl-2-(dimethylamino)methylidene-1-(thiochroman-6-yl)propane-1,3-dione derivatives 4-1)~11-1) tert-Butyl 3-cyclopropyl-2-(thiochorman-6-carbonyl)-3-oxonrinionate derivatives tert-Butyl 3-cyclopropyl-2-(thiochorman-6-carbonyl)-3-oxopropionate derivatives having structural formulae shown in Table 1 (Compounds Nos. V-4-11) were obtained as crude products in the same manner as in Referential Preparation Example 1-1 except that the 6-carboxyl-5-chloro-8-fluoro-4-(2-fluoroethoxy)thiochorman-1,1-dioxide used in Referential Preparation Example 1-1 was replaced with carboxylic acid derivatives as starting materials shown in Table 1. All of the obtained compounds were used as starting materials in Referential Preparation Examples 4-2 to 11-2) without any further purification.

4-2)~11-2) 3-Cyclopropyl-1-(thiochroman-6-yl)propane-1,3-dione derivatives

3-Cyclopropyl-1-(thiochroman-6-yl)propane-1,3-dione derivatives having structural formulae shown in Table 2 (Compounds Nos. VII-4~11) were obtained in the same manner as Referential Preparation Example 1-2 except that the tert-butyl 3-cyclopropyl-2-[5-chloro-8-fluoro-4-(2-fluoroethoxy)thiochroman-1,1-dioxide-6-carbonyl]-3-oxopropionate used in Referential Preparation Example 1-2 was replaced with tert-butyl propionate derivatives shown in Table 1 (Compounds Nos. V-4~V-11). Table 2 shows the yields of the products from the carboxylic acid derivatives as initial starting materials. Further, Table 2 shows NMR data of Compounds VII-4~11.

4-3)~11-3) 3-Cyclopropyl-2-(dimethylamino)methylidene-1-(thiochroman-6-yl)propane-1,3-dione derivatives 3-Cyclopropyl-2-(dimethylamino)methylidene-1-(thiochroman-6-yl)propane-1,3-dione derivatives having structural formulae shown in Table 3 (Compounds Nos. II-4~11) were obtained as crude products in the same manner as in Referential Preparation Example 1-3 except that the 3-cyclopropyl-1-[5-chloro-8-fluoro-4-(2-fluoroethoxy) thiochroman-1,1-dioxide-6-yl]propane-1,3-dione used in Referential Preparation Example 1-3 was replaced with 3-cyclopropyl-1-(thiochroman-6-yl)propane-1,3-dione derivatives shown in Table 2 (Compounds Nos. VII-4~11). The above-obtained compounds were used as starting materials in Preparation Examplea 4 to 11 without any further purification.

TABLE 1-1

| Starting material No. | Starting material | Compound No. | Structural formula |
|---|---|---|---|
| III-1 | [structure] | V-1 | [structure] |
| III-2 | [structure] | V-2 | [structure] |

TABLE 1-1-continued

| Starting material No. | Starting material | Compound No. | Structural formula |
|---|---|---|---|
| III-3 | (Cl, NOCH₃, HO₂C, CH₃, SO₂ substituted thiochromane) | V-3 | (cyclopropyl-CO-CH(CO₂Buᵗ)-CO- linked to Cl, NOCH₃, CH₃, SO₂ thiochromane) |
| III-4 | (Cl, NOCH₃, HO₂C, SO₂ thiochromane) | V-4 | (cyclopropyl-CO-CH(CO₂Buᵗ)-CO- linked to Cl, NOCH₃, SO₂ thiochromane) |
| III-5 | (Cl, NOCH₃, HO₂C, F, SO₂ thiochromane) | V-5 | (cyclopropyl-CO-CH(CO₂Buᵗ)-CO- linked to Cl, NOCH₃, F, SO₂ thiochromane) |
| III-6 | (CF₃, NOCH₃, HO₂C, CH₃, S thiochromane) | V-6 | (cyclopropyl-CO-CH(CO₂Buᵗ)-CO- linked to CF₃, NOCH₃, CH₃, SO₂ thiochromane) |

TABLE 1-2

| Starting material No. | Starting material | Compound No. | Structural formula |
|---|---|---|---|
| III-7 | (CF₃, O, HO₂C, CH₃ (gem-dimethyl), CH₃, S thiochromanone) | V-7 | (cyclopropyl-CO-CH(CO₂Buᵗ)-CO- linked to CF₃, O, CH₃ (gem-dimethyl), CH₃, S thiochromanone) |
| III-8 | (CF₃, OCH₃, HO₂C, CH₃, SO₂ thiochromane) | V-8 | (cyclopropyl-CO-CH(CO₂Buᵗ)-CO- linked to CF₃, OCH₃, CH₃, SO₂ thiochromane) |

TABLE 1-2-continued

| Starting material No. | Starting material | Compound No. | Structural formula |
|---|---|---|---|
| III-9 | (structure) | V-9 | (structure) |
| III-10 | (structure) | V-10 | (structure) |
| III-11 | (structure) | V-11 | (structure) |

TABLE 2-1

| Comp. No. | Yield (%) | Structural formula | NMR (ppm) Solvent: $CDCl_3$ Internal standard: tetramethylsilane |
|---|---|---|---|
| VII-1 | 72 | (structure) | 0.9–1.4(6H, m)1.6–2.0(1H, m) 2.5–2.8(1H, m)3.1–3.5(1H, m) 3.7–4.5(4H, m)4.7–5.0(2H, m) 6.02(1H, s)7.42(1H, d) |
| VII-2 | 80 | (structure) | 0.9–1.3(4H, m)1.48(6H, s) 2.5–2.9(1H, m) 2.73(3H, s)3.52(2H, s) 6.03(1H, s)7.55(1H, s) |

TABLE 2-1-continued

| Comp. No. | Yield (%) | Structural formula | NMR (ppm) Solvent: CDCl₃ Internal standard: tetramethylsilane |
|---|---|---|---|
| VII-3 | 13 | [cyclopropyl-CO-CH₂-CO- attached to thiochroman with Cl, =NOCH₃, CH₃, SO₂] | 0.9–1.3(4H, m)1.6–1.9(1H, m) 2.71(3H, s)3.3–3.4(4H, m) 4.08(3H, s)6.00(1H, s) 7.38 (1H, s) |
| VII-4 | 98 | [cyclopropyl-CO-CH₂-CO- attached to thiochroman with Cl, =NOCH₃, SO₂] | 0.9–1.4(4H, m)1.6–1.9(1H, m) 3.34(4H, br)4.11(3H, s) 6.00(1H, s)7.60(1H, s) 7.94(1H, d) |
| VII-5 | 86 | [cyclopropyl-CO-CH₂-CO- attached to thiochroman with Cl, =NOCH₃, F, SO₂] | 0.9–1.4(4H, m)1.6–1.9(1H, m) 3.2–3.6(4H, m)4.10(3H, s) 6.00(1H, s)7.34(1H, s) |
| VII-6 | 70 | [cyclopropyl-CO-CH₂-CO- attached to thiochroman with CF₃, =NOCH₃, CH₃, S] | 0.8–1.3(4H, m)1.5–1.9(1H, m) 2.38(1H, m)2.8–3.3(4H, br) 4.00(3H, s)5.92(1H, s) 7.30(1H, s) |

TABLE 2-2

| Comp. No. | Yield (%) | Structural formula | NMR (ppm) Solvent: CDCl₃ Internal standard: tetramethylsilane |
|---|---|---|---|
| VII-7 | 68 | [cyclopropyl-CO-CH₂-CO- attached to thiochroman with CF₃, =O, (CH₃)₂, CH₃, S] | 0.8–1.40(4H, m)1.39(6H, s) 1.5–1.9(1H, m)2.36(3H, s) 3.09(2H, s)5.85(2H, s) 7.32(1H, s) |
| VII-8 | 59 | [cyclopropyl-CO-CH₂-CO- attached to thiochroman with CF₃, OCH₃, CH₃, SO₂] | 0.9–1.3(4H, m)1.6–1.9(1H, m) 2.5–2.8(2H, m)2.83(3H, s) 3.2–3.4(1H, m)3.40(3H, s) 3.8–4.1(1H, m)4.7–4.9(1H, m) 5.77(1H, , s)7.37(1H, s) |

TABLE 2-2-continued
| Comp. No. | Yield (%) | Structural formula | NMR (ppm) Solvent: CDCl₃ Internal standard: tetramethylsilane |
|---|---|---|---|
| VII-9 | 40 | 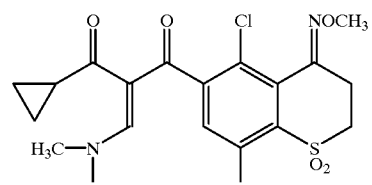 | 0.9–1.3(4H, m)1.48(6H, s) 1.6–2.0(1H, m)3.59(2H, s) 3.87(3H, s)6.47(1H, s) 8.04(1H, s) |
| VII-10 | 91 | | 0.91–1.34(4H, m)1.51(6H, s) 1.6–2.0(1H, m)3.49(2H, s) 3.90(3H, s)6.47(1H, s) 7.77(1H, d)8.09(1H, d) |
| VII-11 | 56 | | 0.9–1.3(4H, m)1.51(6H, s) 1.6–2.0(1H, m)3.49(2H, s) 3.90(3H, s)6.47(1H, s) 7.77(1H, d)8.09(1H, d) |
TABLE 3-1
| Compound No. | Structural formula |
|---|---|
| II-1 | 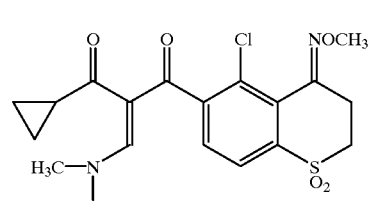 |
| II-2 | |
| II-3 | |
| II-4 | |

TABLE 3-1-continued

| Compound No. | Structural formula |
|---|---|
| II-5 | (structure: cyclopropyl-CO-C(=CH-N(CH3)2)-CO- attached to chloro, fluoro-substituted thiochroman-4-one O-methyloxime with SO2) |
| II-6 | (structure: cyclopropyl-CO-C(=CH-N(CH3)2)-CO- attached to CF3, CH3-substituted thiochroman O-methyloxime) |

TABLE 3-2

| Compound No. | Structural formula |
|---|---|
| II-7 | (structure with CF3, CH3 substituents, thiochroman-4-one with gem-dimethyl) |
| II-8 | (structure with CF3, OCH3, CH3, SO2) |
| II-9 | (structure with OCH3, CH3, Cl, SO2, gem-dimethyl) |
| II-10 | (structure with OCH3, CH3, SO2, gem-dimethyl) |

TABLE 3-2-continued

| Compound No. | Structural formula |
|---|---|
| II-11 | (structure with Cl, OCH3, OCH3, SO2) |

Referential Preparation Example 12

Synthesis of 3-cyclopropyl-2-(dimethylamino)
methylidene-1-(5-chloro-4-methoxy-8-
methylthiochroman-6-yl)propane-1,3-dione 12-1) 3-cyploroiyl-1-(5-chloro-4-methoxy-8-
methylthiochroman-6-yl)propane-1,3-dione 0.88 Gram (22.0 mmol) of 60 wt % sodium hydride/ mineral oil was washed with tetrahydrofuran (THF) to remove the mineral oil. To this was added 15 ml of THF, and the mixture was heated up to 60° C. in a three-necked flask under a nitrogen gas current. Separately, 3.0 g (10.0 mmol) of 5-chloro-6-ethoxycarbonyl-4-methoxy-8-methylthiochroman and 1.68 g (20.0 mmol) of cyclopropyl methyl ketone were dissolved in 15 ml of THF, and the resultant solution was added to the suspension of sodium hydride in THF, and the mixture was allowed to react at a temperature between 50 and 60° C. for 2 hours. After the reaction, water and 5% hydrochloric acid aqueous solution were added, and the mixture was extracted with ethyl acetate. An organic layer was washed with a saturated sodium hydrogencarbonate twice and with a saturated sodium chloride aqueous solution once and dried over anhydrous sodium sulfate, and the solvent was distilled off under reduced pressure to give 2.34 g of a remaining oil. The so-obtained crude product was purified by column chromatography (eluting solution: ethyl acetate/n-hexane, 1:3 v/v) to give 1.37 g (yield 39%) of 3-cyclopropyl-1-(5-chloro-4-methoxy-8-methylthiochroman-6-yl)propane-1,3-dione (Compound No. VII-12) as an end product. Table 4 shows the structural formulae of the starting material and the end product. Table 5 shows the NMR data of the end product.

12-2) 3-cyclopropyl-2-(dimethylamino)methylidene-
1-(5-chloro-4-methoxy-8-methylthiochromnan-6-yl)
propane-1,3-dione 3-Cyclopropyl-2-(dimethylamino)methylidene-1-(5-chloro-4-methoxy-8-methylthiochroman-6-yl)propane-1,3-dione (Compound No. II-12) was obtained as a crude product in the same manner as in Referential Preparation Example 1-3 except that the 3-cyclopropyl-1-[5-chloro-8-fluoro-4-(2-fluoroethoxy)thiochroman-1,1-dioxide-6-yl] propane-1,3-dione used in Referential Preparation Example 1-3 was replaced with 3-cyclopropyl-1-(5-chloro-4-methoxy-8-methylthiochroman-6-yl)propane-1,3-dione (Compound No. VII-12). The above-obtained compound was used as a starting material in Preparation Example 12 without any further purification. Table 6 shows the structural formula of the thus-obtained compound.

Referential Preparation Examples 13–16

Synthesis of 3-cyclopropyl-2-(dimethylamino) methylidene-1-(thiochroman-6-yl)propane-1,3-dione derivatives

13-1)~16-1) 3-cycloprolyl-1-(thiochroman-6-yl) propane-1,3-dione derivatives 3-Cyclopropyl-1-(thiochroman-6-yl)propane-1,3-dione derivatives having structural formulae shown in Table 4 (Compounds Nos. VII-13~16) were obtained in the same manner as in Referential Preparation Example 12-1 except that the 5-chloro-6-ethoxycarbonyl-4-methoxy-8-methylthiochroman used in Referential Preparation Example 12-1 was replaced with carboxylic acid ester derivatives shown in Table 4 as starting materials. Table 4 shows the yields of the end products. Table 5 shows the NMR data of the end compounds.

13-2)~16-2) 3-cyclopronyl-2-(dimethylamino) methylidene-1-(thiochroman-6-yl)prolane-1,3-dione derivatives 3-Cyclopropyl-2-(dimethylamino)methylidene-1-(thiochroman- 6-yl)propane-1,3-dione derivatives having structural formulae shown in Table 6 (Compounds Nos. II-13~16) were obtained as crude products in the same manner as in Referential Preparation Example 1-3 except that the 3-cyclopropyl-1-[5-chloro-8-fluoro-4-(2-fluoroethoxy) thiochroman-1,1-dioxide-6-yl]propane-1,3-dione used in Referential Preparation Example 1-3 was replaced with 3-cyclopropyl-1-(thiochroman-6-yl)propane-1,3-dione derivatives shown in Table 4 (Compounds Nos. VII-13~16). The above-obtained compounds were used as starting materials in Preparation Examples 13 to 16 without any further purification.

TABLE 4

| Starting material No. | Starting material | Yield (%) | Compound No. | Structural formula |
|---|---|---|---|---|
| III'-12 | (5-chloro-6-ethoxycarbonyl-4-methoxy-8-methylthiochroman) | 39 | VII-12 | (3-cyclopropyl-1-(5-chloro-4-methoxy-8-methylthiochroman-6-yl)propane-1,3-dione) |
| III'-13 | (5-chloro-6-ethoxycarbonyl-4-ethoxy-8-methylthiochroman) | 51 | VII-13 | (3-cyclopropyl-1-(5-chloro-4-ethoxy-8-methylthiochroman-6-yl)propane-1,3-dione) |
| III'-14 | (5-chloro-6-ethoxycarbonyl-4-isopropoxy-8-methylthiochroman) | 55 | VII-14 | (3-cyclopropyl-1-(5-chloro-4-isopropoxy-8-methylthiochroman-6-yl)propane-1,3-dione) |
| III'-15 | (5-chloro-6-ethoxycarbonyl-4-(2-fluoroethoxy)-8-methylthiochroman) | 53 | VII-15 | (3-cyclopropyl-1-(5-chloro-4-(2-fluoroethoxy)-8-methylthiochroman-6-yl)propane-1,3-dione) |

TABLE 4-continued

| Starting material No. | Starting material | Yield (%) | Compound No. | Structural formula |
|---|---|---|---|---|
| III'-16 | ethyl 5-(methylthio)-4-methoxy-8-methyl-thiochroman-1,1-dioxide-6-carboxylate | 72 | VII-16 | 1-cyclopropyl-3-[5-(methylthio)-4-methoxy-8-methyl-thiochroman-1,1-dioxide-6-yl]propane-1,3-dione |

TABLE 5

| Compound No. | NMR (ppm) Solvent: CDCl₃ Internal standard: tetramethylsilane |
|---|---|
| VII-12 | 0.8–1.3(4H, m)1.5–1.9(2H, m) 2.24(3H, s)2.3–3.0(2H, m) 3.1–3.6(1H, m)3.49(3H, s) 4.8–4.9(1H, m)6.08(1H, s) 7.27(1H, s) |
| VII-13 | 0.8–1.4(4H, m)1.24(3H, t) 1.5–2.0(2H, m)2.23(3H, s) 2.5–3.0(2H, m)3.2–3.9(3H, m) 4.8–5.0(1H, m)6.08(1H, s) 7.27(1H, s) |
| VII-14 | 0.8–1.3(4H, m)1.22(3H, s) 1.29(3H, s)1.5–2.0(2H, m) 2.26(3H, s)2.5–3.0(2H, m) 3.2–3.6(1H, m)3.8–4.2(1H, m) 5.1–5.3(1H, m)6.06(1H, s) 7.26(1H, s) |
| VII-15 | 0.9–1.3(4H, m)1.5–1.9(2H, m) 2.25(3H, s)2.5–3.0(2H, m) 3.2–3.6(1H, m)3.6–4.4(3H, m) 4.84(1H, t)4.9–5.1(1H, m) 6.07(1H, s)7.28(1H, s) |
| VII-16 | 0.9–1.3(4H, m)1.6–1.9(1H, m) 2.37(3H, s)2.4–2.9(2H, m) 2.77(3H, s)3.1–3.4(1H, m) 3.50(3H, s)3.6–4.1(1H, m) 5.0–5.2(1H, m)6.02(1H, s) 7.35(1H, s) |

TABLE 6

| Compound No. | Structural formula |
|---|---|
| II-12 | (cyclopropyl-CO-C(=CH-N(CH₃)₂)-CO-[5-Cl-4-OCH₃-8-CH₃-thiochroman-6-yl]) |
| II-13 | (cyclopropyl-CO-C(=CH-N(CH₃)₂)-CO-[5-Cl-4-OC₂H₅-8-CH₃-thiochroman-6-yl]) |
| II-14 | (cyclopropyl-CO-C(=CH-N(CH₃)₂)-CO-[5-Cl-4-isopropoxy-8-CH₃-thiochroman-6-yl]) |
| II-15 | (cyclopropyl-CO-C(=CH-N(CH₃)₂)-CO-[5-Cl-4-(2-fluoroethoxy)-8-CH₃-thiochroman-6-yl]) |
| II-16 | (cyclopropyl-CO-C(=CH-N(CH₃)₂)-CO-[5-(SCH₃)-4-OCH₃-8-CH₃-thiochroman-1,1-dioxide-6-yl]) |

Preparation Example 1

1.0 Gram (2.5 mmol) of the crude 3-cyclopropyl-2-(dimethylamino)methylidene-1-[5-chloro-8-fluoro-4-(2-fluoroethoxy)thiochroman-1,1-dioxide-6-yl]propane-1,3- dione (Compound No. II-1) obtained in Referential Preparation Example 1 was dissolved in 5 ml of ethanol, then, 0.2 g of hydroxylamine hydrochloride was added, and the mixture was stirred at room temperature for 8 hours. After the completion of the reaction, the solvent was distilled off under reduced pressure, and the residue was dissolved in methylene chloride. An organic layer was washed with water and dried over anhydrous sodium sulfate, and then the solvent was distilled off under reduced pressure. The resultant residue was purified by silica gel column chromatography (eluting solution; hexane/ethyl acetate= 3:1) to give 0.52 g (yield 48%) of 5-cyclopropyl-4-[5-chloro-8-fluoro-4-(2-fluoroethoxy) thiochroman-1,1-dioxide-6-yl]carbonylisoxazole (Compound No. 1).

Preparation Example 2

5-Cyclopropyl-4-(5-chloro-3,3,8-trimethyl-4-oxothiochroman-1,1-dioxide-6-yl)carbonylisoxazole (Compound No. 2) was obtained at a yield of 77% in the same manner as in Preparation Example 1 except that the 3-cyclopropyl-2-(dimethylamino)methylidene-1-[5-chloro-8-fluoro-4-(2-fluoroethoxy)thiochroman-1,1,-dioxide-6-yl] propane-1,3-dione (Compound No. II-1) used in Preparation Example 1 was replaced with 3-cyclopropyl-2-(dimethylamino)methylidene-1-(5-chloro-3,3,8-trimethyl-4-oxothiochroman-1,1-dioxide-6-yl)propane-1,3-dione (Compound No. II-2) obtained in Referential Preparation Example 2.

Preparation Example 3

5-Cyclopropyl-4-(5-chloro-8-methyl-4-methoxyiminothiochroman-1,1-dioxide-6-yl) carbonylisoxazole (Compound No. 3) was obtained at a yield of 86% in the same manner as in Preparation Example 1 except that the 3-cyclopropyl-2-(dimethylamino) methylidene-1-[5-chloro-8-fluoro-4-(2-fluoroethoxy) thiochroman-1,1-dioxide-6-yl]propane-1,3-dione (Compound No. II-1) used in Preparation Example 1 was replaced with 3-cyclopropyl-2-(dimethylamino) methylidene-1-(5-chloro-8-methyl-4-methoxyiminothiochroman-1,1-dioxide-6-yl)propane-1,3-dione.

Table 7 shows the structural formulae of Compounds Nos. 1, 2 and3, and Table 9shows NMR data, IR data and meltting point measurement results thereof.

Preparation Examples 4–16

5-Cyclopropyl-4-(thiochroman-6-yl)carbonylisoxazole derivatives (Compounds Nos. 4~16) were obtained in the same manner as in Preparation Example 1 except that the 3-cyclopropyl-2-(dimethylamino)methylidene-1-[5-chloro-8-fluoro-4-(2-fluoroethoxy)thiochroman-1,1-dioxide-6-yl] propane-1,3-dione used in Preparation Example 1 was replaced with Compounds shown in Table 3 and Table 6, 3-cyclopropyl-2-(dimethylamino)methylidene-1-(thiochroman-6-yl)propane-1,3-dione derivatives (Compounds Nos. II-4~16). Table 7 shows yields of the end products from Compounds VII-4~16), and Table 9 shows NMR data, IR data and meltting point measurement results thereof.

TABLE 7-1

| Compound No. | Yield (%) | Structural formula |
| --- | --- | --- |
| (1) | 48 | |
| (2) | 66 | |
| (3) | 86 | |

TABLE 7-2

| Compound No. | Yield (%) | Structural formula |
| --- | --- | --- |
| (4) | 62 | |
| (5) | 48 | |
| (6) | 67 | |

TABLE 7-2-continued

| Compound No. | Yield (%) | Structural formula |
|---|---|---|
| (7) | 61 | |
| (8) | 81 | |

TABLE 7-3

| Compound No. | Yield (%) | Structural formula |
|---|---|---|
| (9) | 20 | |
| (10) | 17 | |
| (11) | 59 | |
| (12) | 76 | |

TABLE 7-3-continued

| Compound No. | Yield (%) | Structural formula |
|---|---|---|
| (13) | 69 | |

TABLE 7-4

| Compound No. | Yield (%) | Structural formula |
|---|---|---|
| (14) | 63 | |
| (15) | 66 | |
| (16) | 42 | |

Preparation Example 17

To 0.5 g (1.43 mmol) of the 5-cyclopropyl-4-(5-chloro-4-methoxy-8-methylthiochroman-6-yl) carbonylisoxazole synthesized in Preparation Example 12 were added 1.6 ml of acetic acid and 0.41 g (3.58 mmol) of a 30 wt % hydrogen peroxide aqueous solution, and the mixture was allowed to react at 60° C. for 4.5 hours and then at 70° C. for 1.5 hours. The reaction mixture was allowed to cool, and a sodium hydrogensulfite aqueous solution was added to decompose excessive hydrogen peroxide. The reaction product was extracted with ethyl acetate, and an organic layer was washed with a saturated sodium chloride aqueous solution twice and dried over anhydrous sodium sulfate. The solvent was distilled off under reduced pressure. Remaining acetic acid was removed by heating the reaction product under reduced pressure, to give 0.51 g (yield 90%) of 5-cyclopropyl-4-(5-chloro-4-methoxy-8-methylthiochroman-1,1-dioxide-6-yl)carbonylisoxazole (Compound No. 17) as an end product. Table 8 shows the structural formula of the end compound, and Table 9 shows NMR data, TR data and meltting point measurement result thereof.

Preparation Examples 18–21

Corresponding sulfone compounds (Compounds Nos. 18~21) were obtained in the same manner as in Preparation Example 17 except that the 5-cyclopropyl-4-(5-chloro-4-methoxy-8-methylthiochroman-6-yl)carbonylisoxazole used in Preparation Example 17 was replaced with isoxazole derivatives, Compounds Nos. 15, 6, 7 and 16. Table 8 shows the structural formulae of the end compounds, and Table 9 shows NMR data, IR data and meltting point measurement results thereof.

Preparation Example 22

0.90 Gram (2.3 mmol) of the 5-cyclopropyl-4-(5-methoxy-3,3-dimethyl-4-oxothiochroman-1,1-dioxide-6-yl)carbonylisoxazole (Compound No. 10) obtained in Preparation Example 10 was dissolved in 8 ml of methylene chloride, and then a solution of 0.89 g (2.3 mmol) of boron tribromide in 5 ml of methylene chloride was dropwise added with cooling with ice. Then, the reaction mixture was allowed to warm up to room temperature, and then stirred for about 12 hours. Ice water was poured into the reaction mixture, and the reaction mixture was extracted with methylene chloride. An organic layer was washed with water once and with a saturated sodium chloride aqueous solution once, and dried over anhydrous sodium sulfate, and the solvent was distilled off under reduced pressure to give 0.89 g (yield 95%) of 5-cyclopropyl-4-(5-hydroxy-3,3-dimethyl-4-oxothiochroman-1,1-dioxide-6-yl)carbonylisoxazole (Compound No. 22) as an end product. Table 8 shows the structural formula of the end compound, and Table 9 shows NMR data, IR data and meltting point measurement result thereof.

TABLE 8

| Compound No. | Yield (%) | Structural formula |
|---|---|---|
| (17) | 90 | [structure] |
| (18) | 95 | [structure] |
| (19) | 77 | [structure] |
| (20) | 84 | [structure] |
| (21) | 90 | [structure] |
| (22) | 95 | [structure] |

TABLE 9-1

| Compound No. | IR(cm$^{-1}$) KBr tablet | NMR (ppm) Internal standard: tetramethylsilane Solvent: CDCl$_3$ | Melting point |
|---|---|---|---|
| (1) | 2950, 1680<br>1560, 1400<br>1310, 1120 | 1.1–1.5(4H, m)<br>2.5–3.9(3H, m)<br>3.1–3.5(1H, m)<br>3.6–4.4(4H, m)<br>4.7–5.0(2H, m)<br>7.31(1H, d)8.20(1H, s) | Glass-like substance |
| (2) | 3000, 1735<br>1685, 1580<br>1335, 1155 | 1.2–1.7(4H, m)1.49(6H, s)<br>2.5–2.8(1H, m)<br>2.76(3H, s)3.56(2H, s)<br>7.41(1H, s)<br>8.18(1H, s) | Glass-like substance |
| (3) | 2950, 1650<br>1580, 1410<br>1310, 1150<br>1040 | 1.1–1.5(4H, m)<br>2.5–2.8(1H, m)<br>2.75(3H, s)3.3–3.5(4H, m)<br>4.07(3H, s)7.26(1H, s)<br>8.21(1H, s) | Glasslike substance |
| (4) | 2950, 1670<br>1590, 1420<br>1320, 1160<br>1050 | 1.1–1.5(4H, m)<br>2.5–2.8(1H, m)<br>3.38(4H, br)4.10(3H, s)<br>7.50(1H, d)8.03(1H, d)<br>8.18(1H, s) | Glass-like substance |

TABLE 9-1-continued

| Compound No. | IR(cm$^{-1}$) KBr tablet | NMR (ppm) Internal standard: tetramethylsilane Solvent: CDCl$_3$ | Melting point |
|---|---|---|---|
| (5) | 2980, 1690 1580, 1420 1360, 1180 1070 | 1.2–1.5(4H, m) 2.5–2.9(1H, m) 3.2–3.6(4H, m)4.09(3H, s) 7.23(1H, d)8.20(1H, s) | Glass-like substance |
| (6) | 2960, 1720 1650, 1560 1260, 1140 1040 | 1.1–1.4(4H, m)2.40(3H, s) 2.4–2.8(1H, m) 2.8–3.3(4H, m) 3.98(3H, s)7.19(1H, s) 8.22(1H, s) | Glass-like substance |

TABLE 9-2

| Compound No. | IR(cm$^{-1}$) KBr tablet | NMR (ppm) Internal standard: tetramethylsilane Solvent: CDCl$_3$ | Melting point |
|---|---|---|---|
| (7) | 3000, 1720 1680, 1590 1300, 1270 1160 | 1.15–1.5(4H, m)1.40(6H, s) 2.5–2.8(1H, m)2.38(3H, s) 3.14(2H, s)7.21(1H, s) 8.17(1H, s) | Glass-like substance |
| (8) | 3000, 1700 1600, 1320 1150 | 1.1–1.4(4H, m) 2.5–2.8(3H, m) 2.85(3H, s)3.2–3.4(1H, m) 3.42(3H, s)3.8–4.2(1H, m) 4.7–4, 9(1H, m)7.29(1H, s) 8.17(1H, s) | Glass-like substance |
| (9) | 2920, 1705 1645, 1420 1320, 1140 1050 | 1.2–1.8(4H, m)1.50(6H, s) 2.6–2.9(1H, m)3.62(2H, s) 3.76(3H, s)7.70(1H, s) 8.18(1H, s) | Glass–like substance |
| (10) | 3000, 1720 1670 1320 1140 | 1.2–1.7(4H, m)1.53(6H, s) 2.6–2.9(1H, m)3.55(2H, s) 3.81(3H, s)7.73(1H, d) 7.84(1H, d)8.19(1H, s) | Glass-like substance |
| (11) | 2940, 1680 1570, 1310 1120, 1060 | 1.2–1.5(4H, m) 2.4–2.8(3H, m) 3.1–3.4(1H, m)3.50(3H, s) 3.6–4.1(1H, m)4.00(3H, s) 4.6–4.8 (1H, m)7.02(1H, s) 8.19(1H, s) | Glass-like substance |
| (12) | — | 1.15–1.4(4H, m) 1.5–1.9(1H, m) 2.26(3H, s)2.5–3.6(4H, m) 3.49(3H, s)4.7–4.9(1H, m) 7.12(1H, s)8.22(1H, s) | Glass-like substance |

TABLE 9-3

| Compound No. | IR(cm$^{-1}$) KBr tablet | NMR (ppm) Internal standard: tetramethylsilane Solvent: CDCl$_3$ | Melting point |
|---|---|---|---|
| (13) | 2950, 1665 1590, 1420 1100, 1005 | 1.1–1.4(4H, m)1.24(3H, t) 1.5–1.9(1H, m)2.25(3H, s) 2.5–3.0(3H, m) 3.2–3.9 (3H, m) 4.8–5.0(1H, m)7.11(1H, s) 8.24(1H, s) | Glass-like substance |
| (14) | 2980, 1670 1590, 1390 1050 | 1.1–1.4(4H, m)1.21(3H, s) 1.28(3H, s)1.5–1.9(1H, m) 2.24(3H, s)2.5–3.0(3H, m) 3.3–3.7(1H, m) 3.8–4.2(1H, m) 7.10(1H, s)8.23(1H, s) | Glass-like substance |

TABLE 9-3-continued

| Compound No. | IR(cm$^{-1}$) KBr tablet | NMR (ppm) Internal standard: tetramethylsilane Solvent: CDCl$_3$ | Melting point |
|---|---|---|---|
| (15) | 2940, 1650 1580, 1400 1095, 1030 1000 | 1.1–1.4(4H, m)1.5–2.0(1H, m) 2.26(3H, s)2.4–3.0(3H, m) 2–4.2(3H, m)4.30(1H, t) 4.83(1H, t)4.9–5.1(1H, m) 7.13(1H, s)8.23(1H, s) | Glass-like substance |
| (16) | 2940, 1660 1580, 1290 1120, 1070 | 1.1–1.4(4H, m)2.31(3H, s) 2.3–2.9(3H, m)2.80(3H, s) 3.50(3H, s)3.1–3.5(1H, m) 3.6–4.1(1H, m) 5.0–5.2(1H, m) 7.25(1H, s)8.12(1H, s) | Glass-like substance |
| (17) | 2940, 1665 1590, 1305 1285, 1125 1070 | 1.2–1.5(4H, m)1.76(1H, m) 2.5–2.9(3H, m)2.78(3H, s) 3.1–3.4(1H, m) 3.7–4.1(1H, m) 4.7–4.9(1H, m)7.30(1H, s) 8.17(1H, s) | Glass-like substance |
| (18) | 2970, 1680 1580, 1320 1140, 1050 | 1.2–1.4(4H, m) 2.4–2.9(3H, m) 2.78(3H, s)3.1–3.4(1H, m) 3.7–4.4(4H, m) 4.7–5.0(2H, m) 7.31(1H, s)8.18(1H, s) | Glass-like substance |

TABLE 9-4

| Compound No. | IR(cm$^{-1}$) KBr tablet | NMR (ppm) Internal standard: tetramethylsilane Solvent: CDCl$_3$ | Melting point |
|---|---|---|---|
| (19) | 2960, 1690 1595, 1330 1300, 1155 1060 | 1.2–1.5(4H, m) 2.4–2.8(1H, m) 2.82(3H, s)3.2–3.6(4H, m) 4.04(3H, s)7.35(1H, s) 8.17(1H, s) | 216.1–218.6 |
| (20) | 2960, 1715 1675, 1565 1305, 1125 | 1.2–1.5(4H, m)1.53(6H, s) 2.5–2.8(1H, m)2.83(3H, s) 3.62(2H, s)7.46(1H, s) 8.13(1H, s) | Glass-like substance |
| (21) | 2950, 1665 1580, 1305 1130, 1075 | 1.15–1.5(4H, m) 2.4–2.9(3H, m) 2.86(3H, s)3.1–4.0(2H, m) 3.37(3H, s)3.51(3H, s) 5.8–6.0(1H, m)7.28(1H, s) 8.18(1H, s) | Glass-like substance |
| (22) | 3400, 2980 1650, 1580 1415, 1320 1135 | 1.2–1.5(4H, m)1.6(6H, s) 2.7–3.1(1H, m)3.60(2H, s) 7.65(1H, d)7.87(1H, d) 8.22(1H, s)13.2(1H, s) | Glass-like substance |

The usefulness of the compounds of the present invention as herbicides will be specifically explained hereinafter with reference to the following experiments.

Herbicide Examples and Herbicide Comparative Examples (1) Preparation of Herbicides 97 Parts by weight of talc (trade name: Zeaklite) as a carrier, 1.5 parts by weight of alkylarylsulfonic acid (trade name: Neoplex, supplied by Kao-Atlas K. K.) as a surfactant and 1.5 parts by weight of a nonionic and anionic surfactant (tradename: Sorpol 800A, supplied by Toho Chemical Co., Ltd.) were uniformly pulverized and mixed to prepare a carrier for a wettable powder.

90 Parts by weight of the above carrier for a wettable powder and 10 parts by weight of one of the compounds of the present invention obtained in the above Preparation Examples 1 and 2 (or 10 parts by weight of one of the following compounds (A) and (B) for Comparative Examples) were uniformly pulverized and mixed to obtain herbicides.

The following compound (A) for Comparative Example is disclosed in WO93/18031, and the following compound (B) for Comparative Example is disclosed in EP95/0636622. The compounds (A) and (B) have the following structures.

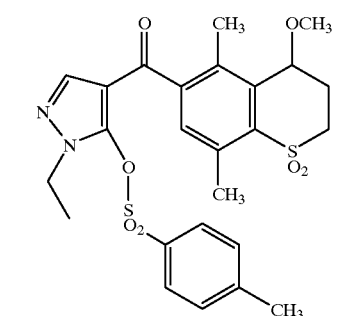

(A)

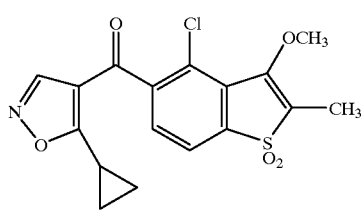

(B)

The herbicidal efficacy and phytotoxcity to crops were shown on the basis of the following ratings.

| (Ratings) | |
|---|---|
| Herbicidal efficacy | Ratio of remaining plant weight to non-treated (%) |
| 0 | 81–100 |
| 1 | 61–80 |
| 2 | 41–60 |
| 3 | 21–40 |
| 4 | 1–20 |
| 5 | 0 |
| Phytotoxicity to crops | Ratio of remaining plant weight to non-treated (%) |
| − | 100 |
| ± | 95–99 |
| + | 90–94 |
| ++ | 80–89 |
| +++ | 0–79 |

The above ratio of remaining plant weight to non-treated was determined on the basis of the ratio of remaining plant weight to non-treated=(remaining plant weight in treated plot/remaining plant weight in non-treated plot)×100.

(2) Pre-emergence Treatment Test 1

Seeds of weeds such as cocklebur, velvetleaf, Ivyleaf morningglory, jimsonweed, barnyardgrass and large crabgrass and seeds of corn, sorgo and cotton were sown in 1/5,000-are Wagner pots filled with upland soil, and covered with upland soil. Then, a predetermined amount of the herbicide prepared in the above (1) was suspended in water and uniformly sprayed onto the soil surface. Then, the seeds were grown in a greenhouse, and on 20th day after the treatment, the herbicide was evaluated for herbicidal efficacy and phytotoxicity to the crops. Table 10 shows the results.

TABLE 10

| Com'd No. | Dosage (g$^{a.i.}$/ha) | Herbicidal efficacy | | | | | | Phytotoxicity | | |
|---|---|---|---|---|---|---|---|---|---|---|
| | | A | B | C | D | E | F | G | H | I |
| (1) | 300 | 5 | 5 | 5 | 5 | 5 | 5 | − | − | + |
| (2) | 300 | 4 | 5 | 4 | 5 | 5 | 5 | − | + | − |
| (A) | 300 | 5 | 5 | 0 | 5 | 5 | 5 | − | +++ | +++ |
| (B) | 300 | 0 | 1 | 0 | 1 | 0 | 0 | − | − | − |

$^{a.i.}$ = active ingredient
A = cocklebur, B = velvetleaf, C = Ivyleaf morningglory, D = Jomsonweed, E = large crabgrass, F = barnyardgrass, G = corn, H = sorgo, I = cotton Table 10 shows the following. According to the herbicides of the present invention, Compound No. 1 does not cause any phytotoxicity on corn and sorgo, and Compound No. 2 does not cause any phytotoxicity on corn and cotton. Further, it is shown that Compounds Nos. 1 and 2 can selectively control a broad range of upland weeds at a low dosage. In contrast, the comparative compound (A) has poor safety to cotton and sorgo, and has poor efficacy on Ivyleaf morningglory. It is further shown that the comparative compound (B) is generally poor in herbicidal efficacy.

(3) Pre-emergence Treatment Test 2

Seeds of weeds such as common chickweed, wild chamomile, violet, shepherdspurse, annual bluegrass, blackgrass and wildoat and seeds of wheat and barley were sown in 1/5,000-are Wagner pots filled with upland soil, and covered with upland soil. Then, a predetermined amount of the herbicide prepared in the above (1) was suspended in water and uniformly sprayed onto the soil surface. Then, the seeds were grown in a greenhouse, and on 30th day after the treatment, the herbicide was evaluated for herbicidal efficacy and phytotoxicity to the crops. Table 11 shows the results.

TABLE 11

| Com'd No. | Dosage (g$^{a.i.}$/ha) | Herbicidal efficacy | | | | | | Phytotoxicity | |
|---|---|---|---|---|---|---|---|---|---|
| | | A | B | C | D | E | F | G | H | I |
| (1) | 320 | 5 | 5 | 5 | 3 | 4 | 2 | 4 | ± | − |
| (B) | 320 | 1 | 0 | 0 | 1 | 0 | 0 | 0 | − | − |

$^{a.i.}$ = active ingredient
A = common chickweed, B = violet, C = wild chamomile, D = shepherdspurse, E = annual bluegrass, F = blackgrass, G = wildoat, H = wheat, I = barley Table 11 shows the following. The herbicide of the present invention causes no phytotoxicity on wheat and barley and can selectively control a broad range of upland winter weeds at a low dosage. In contrast, the comparative herbicide (B) is poor in general herbicidal efficacy, and in particular, it has poor herbicidal efficacy on wild chamomile, violet, annual bluegrass, blackgrass and wildcat.

(4) Post-emergence Treatment Test 1

Seeds of weeds such as cocklebur, velvetleaf, Ivyleaf morningglory, jimsonweed, barnyardgrass and large crabgrass and seeds of corn and sorgo were sown in 1/5,000-are Wagner pots filled with upland soil, and covered with upland soil. The seeds were grown in a greenhouse, and at the stage of 3~4 leaves of these plants, a predetermined amount of the herbicide prepared in the above (1) was suspended in water and uniformly sprayed onto leaf and stalk portions at a rate of 2,000 l/ha. Then, the plants were grown in the greenhouse, and on 30th day after the treatment, the herbicide was evaluated for herbicidal efficacy and phytotoxicity to the crops. Table 12 shows the results.

TABLE 12

| Com'd No. | Dosage (g^{a.i.}/ha) | Herbicidal efficacy | | | | | | | Phytotoxicity | |
|---|---|---|---|---|---|---|---|---|---|---|
| | | A | B | C | D | E | F | G | H |
| (1) | 300 | 4 | 5 | 4 | 5 | 3 | 3 | – | – |
| (2) | 300 | 5 | 5 | 5 | 5 | 3 | 3 | – | – |
| (A) | 300 | 5 | 5 | 0 | 5 | 4 | 4 | – | +++ |
| (B) | 300 | 0 | 1 | 1 | 1 | 1 | 0 | – | – | a.i. = active ingredient
A = cocklebur, B = velvetleaf, C = Ivyleaf morningglory, D = Jomsonweed, E = large crabgrass, F = barnyardgrass, G = corn, H = sorgo Table 12 shows the following. The herbicide of the present invention does not cause any phytotoxicity on corn and sorgo and can selectively control a broad range of upland soil weeds at a low dosage. In contrast, the comparative compound (B) is poor in general herbicidal efficacy.

(5) Pre-emergence Treatment Test 3

Seeds of weeds such as cocklebur, velvetleaf, Jimsonweed, black nightshade and barnyardgrass and seeds of corn were sown in 1/5,000-are Wagner pots filled with upland soil and covered with upland soil. Then, a predetermined amount of the herbicide prepared in the above (1) was suspended in water and uniformly sprayed onto the soil surface. Then, the seeds were grown in a greenhouse, and on 20th day after the treatment, the herbicide was evaluated for herbicidal efficacy and phytotoxicity to the crops. Table 13 shows the results.

TABLE 13

| Com'd No. | Dosage (g^{a.i.}/ha) | Herbicidal efficacy | | | | | Phytotoxicity |
|---|---|---|---|---|---|---|---|
| | | A | B | C | D | E | Corn |
| 1 | 150 | 4 | 5 | 5 | 5 | 5 | – |
| 3 | 150 | 4 | 5 | 5 | 5 | 5 | – |
| 4 | 150 | 5 | 5 | 5 | 5 | 5 | – |
| 8 | 150 | 3 | 5 | 5 | 5 | 4 | – |
| 9 | 150 | 2 | 3 | 5 | 5 | 4 | – |
| 10 | 150 | 4 | 4 | 5 | 5 | 4 | – |
| 13 | 150 | 3 | 5 | 5 | 5 | 4 | – |
| 18 | 150 | 3 | 5 | 5 | 5 | 4 | – |
| 20 | 150 | 4 | 4 | 5 | 5 | 4 | – |
| (B) | 150 | 0 | 0 | 0 | 0 | 0 | – | a.i. = active ingredient, A = cocklebur, B = velvetleaf, C = jimsonweed, D = black nightshade, E = barnyardgrass Table 13 shows the following. The herbicides of the present invention do not cause phytotoxicity on corn, and can selectively control a broad range of upland weeds at a low dosage. In contrast, the comparative compound (B) is poor in the efficacy on all the weeds tested.

(6) Upland Soil Post-emergence Treatment Test 2

Seeds of weeds such as cocklebur, velvetleaf, jimsonweed, black nightshade, barnyardgrass and large crabgrass and seeds of corn were sown in 1/5,000-are Wagner pots filled with upland soil, and covered with upland soil. The seeds were grown in a greenhouse, and at the stage of 3~4 leaves of these plants, a predetermined amount of the herbicide prepared in the above (1) was suspended in water and uniformly sprayed onto leaf and stalk portions at a rate of 2,000 l/ha. Then, the plants were grown in the greenhouse, and on 30th day after the treatment, the herbicide was evaluated for herbicidal efficacy and phytotoxicity to the crops. Table 14 shows the results.

TABLE 14

| Com'd No. | Dosage (g^{a.i.}/ha) | Herbicidal efficacy | | | | | | Phytotoxicity |
|---|---|---|---|---|---|---|---|---|
| | | A | B | C | D | E | F | Corn |
| 4 | 300 | 5 | 5 | 5 | 5 | 5 | 5 | – |
| 12 | 300 | 5 | 5 | 5 | 5 | 5 | 4 | – |
| 13 | 300 | 5 | 5 | 5 | 5 | 4 | 4 | – |
| 17 | 300 | 5 | 5 | 5 | 5 | 5 | 4 | – |
| 20 | 300 | 5 | 5 | 5 | 5 | 4 | 4 | – |
| (B) | 300 | 0 | 1 | 1 | 0 | 0 | 1 | – | a.i. = active ingredient, A = cocklebur, B = velvetleaf, C = jimsonweed, D = black nightshade, E = barnyardgrass, F = large crabgrass Table 14 shows the following. he herbicides of the present invention do not cause phytotoxicity on corn, and can selectively control a broad range of upland weeds at a low dosage. In contrast, the comparative compound (B) is poor in the efficacy on all the weeds tested.

INDUSTRIAL UTILITY

The isoxazole derivative of the present invention causes no phytotoxicity on corn, sorgo, cotton, wheat, barley, and the like, and it can selectively control a broad range of upland weeds such as grass weeds and broad-leaved weeds at a low dosage and is remarkably useful as an active ingredient for a herbicide against upland weeds.

We claim:

1. The isoxazole derivative of the general formula (I), (I)

wherein $R^1$ is a $C_1$–$C_6$ alkyl group or a $C_3$–$C_6$ cycloalkyl group, $R^2$ is a hydrogen atom or a $C_1$–$C_4$ alkoxycarbonyl group, each of $R^3$ to $R^6$ is independently a hydrogen atom or a $C_1$–$C_4$ alkyl group, or $R^3$ and $R^5$ may bond to each other and form a double bond, n is an integer of 0, 1 or 2, X is a halogen atom, a $C_1$–$C_4$ haloalkyl group, a $C_1$–$C_4$ alkoxy group, a $C_1$–$C_4$ haloalkoxy group, a $C_1$–$C_4$ alkylthio group, a $C_1$–$C_4$ alkylsulfonyl group, a $C_1$–$C_4$ haloalkylthio group, a $C_1$–$C_4$ haloalkylsulfonyl group, a $C_1$–$C_4$ (di)alkylamino group, a (bis) $C_1$–$C_4$ haloalkylamino group, an amino group, a hydroxyl group or a nitro group, Y is a hydrogen atom, a $C_1$–$C_4$ alkyl group, a $C_1$–$C_4$ alkoxy group or a halogen atom, and Z is a group of (a)

-continued

(b)

in which each of $R^7$ and $R^8$ is independently a hydrogen atom, a $C_1$–$C_4$ alkyl group or a $C_1$–$C_4$ alkoxy group, provided that when $R^7$ and/or $R^8$ are/is $C_1$–$C_4$ alkyl group(s) or $C_1$–$C_4$ alkoxy group(s), 1 to 9 hydrogen atoms thereof may be replaced with 1 to 9 halogen atoms, further when the number of carbon atoms thereof is $C_2$–$C_4$, the substituent(s) may have unsaturated bond(s), and that when both $R^7$ and $R^8$ are $C_1$–$C_4$ alkyl groups or $C_1$–$C_4$ alkoxy groups, then $R^7$ and $R^8$ may form a 3- to 7-membered ring in which carbon atoms of the substituents bond to each other, and $R^9$ is an oxygen atom, a sulfur atom or a $C_1$–$C_4$ alkoxyimino group, provided that when $R^9$ is a $C_1$–$C_4$ alkoxyimino group, 1 to 9 hydrogen atoms thereof may be replaced with 1 to 9 halogen atoms, further when the number of carbon atoms thereof is $C_2$–$C_4$, the substituent may have unsaturated bond(s).

2. The isoxazole derivative of claim 1, which has the general formula (Ia),

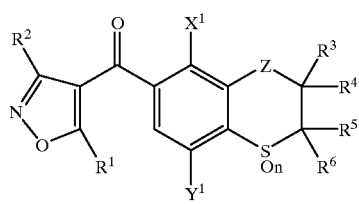
(Ia)

wherein $R^1$ is a $C_1$–$C_6$ alkyl group or a $C_3$–$C_6$ cycloalkyl group, $R^2$ is a hydrogen atom or a $C_1$–$C_4$ alkoxycarbonyl group, each of $R^3$ to $R^6$ is independently a hydrogen atom or a $C_1$–$C_4$ alkyl group, or $R^3$ and $R^5$ may bond to each other and form a double bond, n is an integer of 0, 1 or 2, $X^1$ is a halogen atom, a $C_1$–$C_4$ haloalkyl group, a $C_1$–$C_4$ alkoxy group, a $C_1$–$C_4$ haloalkoxy group, a $C_1$–$C_4$ alkylthio group, a $C_1$–$C_4$ alkylsulfonyl group or nitro group, $Y^1$ is a hydrogen atom, a $C_1$–$C_4$ alkyl group or a halogen atom, and Z is a group of

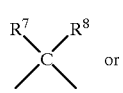
(a)

(b)

in which each of $R^7$ and $R^8$ is independently a hydrogen atom, a $C_1$–$C_4$ alkyl group or a $C_1$–$C_4$ alkoxy group, provided that when $R^7$ and/or $R^8$ are/is $C_1$–$C_4$ alkyl group(s) or $C_1$–$C_4$ alkoxy group(s), 1 to 9 hydrogen atoms thereof may be replaced with 1 to 9 halogen atoms, further when the number of carbon atoms thereof is $C_2$–$C_4$, the substituent(s) may have unsaturated bond(s), and that when both $R^7$ and $R^8$ are $C_1$–$C_4$ alkyl groups or $C_1$–$C_4$ alkoxy groups, then $R^7$ and $R^8$ may form a 3-to 7-membered ring in which carbon atoms of the substituents bond to each other, and $R^9$ is an oxygen atom, a sulfur atom or a $C_1$–$C_4$ alkoxyimino group, provided that when $R^9$ is a $C_1$–$C_4$ alkoxyimino group, 1 to 9 hydrogen atoms thereof may be replaced with 1 to 9 halogen atoms, further when the number of carbon atoms thereof is $C_2$–$C_4$, the substituent may have unsaturated bond(s).

3. The isoxazole derivative of the general formula (Ib),

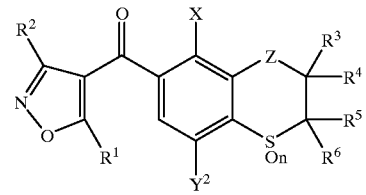
(Ib)

wherein $R^1$ is a $C_1$–$C_6$ alkyl group or a $C_3$–$C_6$ cycloalkyl group, $R^2$ is a hydrogen atom or a $C_1$–$C_4$ alkoxycarbonyl group, each of $R^3$ to $R^5$ is independently a hydrogen atom or a $C_1$–$C_4$ alkyl group, or $R^3$ and $R^5$ may bond to each other and form a double bond, n is an integer of 0, 1 or 2, X is a halogen atom, a $C_1$–$C_4$ haloalkyl group, a $C_1$–$C_4$ alkoxy group, a $C_1$–$C_4$ haloalkoxy group, a $C_1$–$C_4$ alkylthio group, a $C_1$–$C_4$ alkylsulfonyl group, a $C_1$–$C_4$ haloalkylthio group, a $C_1$–$C_4$ haloalkylsulfonyl group, a $C_1$–$C_4$ (di)alkylamino group, a (bis)$C_1$–$C_4$ haloalkylamino group, an amino group, a hydroxy group or a nitro group, $Y^2$ is a $C_1$–$C_4$ alkyl group, a $C_1$–$C_4$ alkoxy group or a halogen atom, and Z is a group of

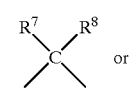
(a)

(b)

in which each of $R^7$ and $R^8$ is independently a hydrogen atom, a $C_1$–$C_4$ alkyl group or a $C_1$–$C_4$ alkoxy group, provided that when $R^7$ and/or $R^8$ are/is $C_1$–$C_4$ alkyl group(s) or $C_1$–$C_4$ alkoxy group(s), 1 to 9 hydrogen atoms thereof may be replaced with 1 to 9 halogen atoms, further when the number of carbon atoms thereof is $C_2$–$C_4$, the substituent(s) may have unsaturated bond(s), and that when both $R^7$ and $R^8$ are $C_1$–$C_4$ alkyl groups or $C_1$–$C_4$ alkoxy groups, then $R^7$ and $R^8$ may form a 3- to 7-membered ring in which carbon atoms of the substituents bond to each other, and $R^9$ is an oxygen atom, a sulfur atom or a $C_1\sim C_4$ alkoxyimino group, provided that when $R^9$ is a $C_1\sim C_4$ alkoxyimino group, 1 to 9 hydrogen atoms thereof may be replaced with 1 to 9 halogen atoms, further when the number of carbon atoms thereof is $C_2\sim C_4$, the substituent may have unsaturated bond(s).

4. The isoxazole derivative of claim 2, which has the general formula (Ic),

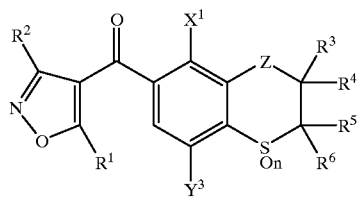
(Ic)

wherein $R^1$ is a $C_1\sim C_6$ alkyl group or a $C_3\sim C_6$ cycloalkyl group, $R^2$ is a hydrogen atom or a $C_1\sim C_4$ alkoxycarbonyl group, each of $R^3$ to $R^6$ is independently a hydrogen atom or a $C_1\sim C_4$ alkyl group, or $R^3$ and $R^5$ may bond to each other and form a double bond, n is an integer of 0, 1 or 2, $X^1$ is a halogen atom, a $C_1\sim C_4$ haloalkyl group, a $C_1\sim C_4$ alkoxy group, a $C_1\sim C_4$ haloalkoxy group, an $C_1\sim C_4$ alkylthio group, a $C_1\sim C_4$ alkylsulfonyl group or a nitro group, $Y^3$ is a $C_1\sim C_4$ alkyl group or a halogen atom, and Z is a group of

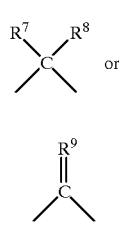
(a)

or (b)

in which each of $R^7$ and $R^8$ is independently a hydrogen atom, a $C_1\sim C_4$ alkyl group or a $C_1\sim C_4$ alkoxy group, provided that when $R^7$ and/or $R^8$ are/is $C_1\sim C_4$ alkyl group(s) or $C_1\sim C_4$ alkoxy group(s), 1 to 9 hydrogen atoms thereof may be replaced with 1 to 9 halogen atoms, further when the number of carbon atoms thereof is $C_1\sim C_4$, the substituent(s) may have unsaturated bond(s), and that when both $R^7$ and $R^8$ are $C_1\sim C_4$ alkyl groups or $C_1\sim C_4$ alkoxy groups, then $R^7$ and $R^8$ may form a 3- to 7-membered ring in which carbon atoms of the substituents bond to each other, and $R^9$ is an oxygen atom, a sulfur atom or a $C_1\sim C_4$ alkoxyimino group, provided that when $R^9$ is a $C_1\sim C_4$ alkoxyimino group, 1 to 9 hydrogen atoms thereof may be replaced with 1 to 9 halogen atoms, further when the number of carbon atoms thereof is $C_2\sim C_4$, the substituent may have unsaturated bond(s).

5. The isoxazole derivative of claim 1, which has the general formula (Id),

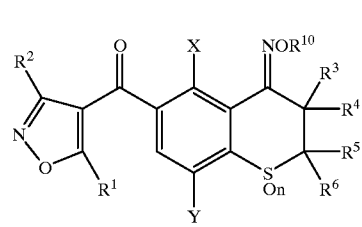
(Id)

wherein $R^1$ is a $C_1\sim C_6$ alkyl group or a $C_3\sim C_6$ acycloalkyl group, $R^2$ is a hydrogen atom or a $C_1\sim C_4$ alkoxycarbonyl group, each of $R^3$ to $R^6$ is independently a hydrogen atom or a $C_1\sim C_4$ alkyl group, or $R^3$ and $R^5$ may bond to each other and form a double bond, n is an integer of 0, 1 or 2, X is a halogen atom, a $C_1\sim C_4$ haloalkyl group, a $C_1\sim C_4$ alkoxy group, a $C_1\sim C_4$ haloalkoxy group, a $C_1\sim C_4$ alkylthio group, a $C_1\sim C_4$ alkylsulfonyl group, a $C_1\sim C_4$ haloalkylthio group, a $C_1\sim C_4$ haloalkylsulfonyl group, a $C_1\sim C_4$ (di)alkylamino group, a (bis)$C_1\sim C_4$ haloalkylamino group, an amino group, a hydroxy group or a nitro group, Y is a hydrogen atom, a $C_1\sim C_4$ alkyl group, a $C_1\sim C_4$ alkoxy group or a halogen atom, and $R^{10}$ is a $C_1\sim C_4$ alkyl group, in which 1 to 9 hydrogen atoms, thereof may be replaced with 1 to 9 halogen atoms, and provided that when the number of carbon atoms thereof is $C_2\sim C_4$, the substituent may have unsaturated bond(s).

6. The isoxazole derivative of claim 2, which has the general formula (Ie),

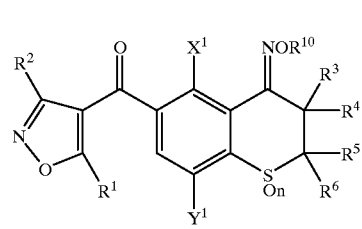
(Ie)

wherein $R^1$ is a $C_1\sim C_6$ alkyl group or a $C_3\sim C_6$ acycloalkyl group, $R^2$ is a hydrogen atom or a $C_1\sim C_4$ alkoxycarbonyl group, each of $R^3$ to $R^6$ is independently a hydrogen atom or a $C_1\sim C_4$ alkyl group, or $R^3$ and $R^5$ may bond to each other and form a double bond, n is an integer of 0, 1 or 2, $X^1$ is a halogen atom, a $C_1\sim C_4$ haloalkyl group, a $C_1\sim C_4$ alkoxy group, a $C_1\sim C_4$ haloalkoxy group, a $C_1\sim C_4$ alkylthio group, a $C_1\sim C_4$ alkylsulfonyl group or nitro group, $Y^1$ is a hydrogen atom, a $C_1\sim C_4$ alkyl group or a halogen atom, and $R^{10}$ is a $C_1\sim C_4$ alkyl group, in which 1 to 9 hydrogen atoms thereof may be replaced with 1 to 9 halogen atoms, and provided that when the number of carbon atoms thereof is $C_2\sim C_4$, the substituent may have unsaturated bond(s).

7. The isoxazole derivative of claim 1, wherein, in the general formula (I), $R^1$ is a cyclopropyl group and $R^2$ is a hydrogen atom.

8. The isoxazole derivative of claim 1, wherein, in the general formula (I), each of $R^3$, $R^4$, $R^5$ and $R^6$ is a hydrogen atom or methyl.

9. The isoxazole derivative of claim 1, wherein, in the general formula (I), X is a chlorine atom, —$CHF_2$, —$CF_3$, —$OCF_3$, —$OCH_3$, —$OCHF_2$, —$SCHF_2$, —$SCF_3$, —$SO_2CF_3$, —$N(CH_3)_2$ or a nitro group.

10. The isoxazole derivative of claim 1, wherein, in the general formula (I), Y is a hydrogen atom, methyl, a fluorine atom or a chlorine atom.

11. The isoxazole derivative of claim 1, wherein, in the general formula (I), n is 0 or 2.

12. The isoxazole derivative of claim 2, wherein, in the general formula (Ia), $R^1$ is a cyclopropyl group and $R^2$ is a hydrogen atom.

13. The isoxazole derivative of claim 2, wherein, in the general formula (Ia), each of $R^3$, $R^4$, $R^5$ and $R^6$ is a hydrogen atom or methyl.

14. The isoxazole derivative of claim 2, wherein, in the general formula (Ia), $X^1$ is a chlorine atom, —$CHF_2$, —$CF_3$, —$OCF_3$, —$OCH_3$ or a nitro group.

15. The isoxazole derivative of claim 2, wherein, in the general formula (Ia), $Y^1$ is a hydrogen atom, methyl, a fluorine atom or a chlorine atom.

16. The isoxazole derivative of claim 2, wherein, in the general formula (Ia), n is 0 or 2.

17. The isoxazole derivative of claim 5, wherein, in the general formula (Id), $R^{10}$ is methyl.

18. The isoxazole derivative of claim 6, wherein, in the general formula (Ie), $R^{10}$ is methyl.

19. A herbicide containing, as anactive ingredient, the isoxazole derivative of the general formula (I) recited in claim 1.

20. A herbicide containing, as an active ingredient, the isoxazole derivative of the general formula (Ia) recited in claim 2.

* * * * *